US012751949B2

(12) United States Patent
Angst et al.

(10) Patent No.: US 12,751,949 B2
(45) Date of Patent: Oct. 6, 2026

(54) CRYSTALLINE FORMS OF A BTK INHIBITOR

(71) Applicant: NOVARTIS AG, Basel (CH)

(72) Inventors: Daniela Angst, Basel (CH); Andreas Kordikowski, Binningen (CH)

(73) Assignee: NOVARTIS AG, Basel (CH)

( * ) Notice: Subject to any disclaimer, the term of this patent is extended or adjusted under 35 U.S.C. 154(b) by 1298 days.

(21) Appl. No.: 17/612,716

(22) PCT Filed: May 20, 2020

(86) PCT No.: PCT/IB2020/054752
§ 371 (c)(1),
(2) Date: Nov. 19, 2021

(87) PCT Pub. No.: WO2020/234779
PCT Pub. Date: Nov. 26, 2020

(65) Prior Publication Data

US 2025/0268895 A1 Aug. 28, 2025

Related U.S. Application Data

(60) Provisional application No. 62/851,986, filed on May 23, 2019.

(51) Int. Cl.
*A61K 31/505* (2006.01)
*C07D 239/47* (2006.01)

(52) U.S. Cl.
CPC .......... *A61K 31/505* (2013.01); *C07D 239/47* (2013.01)

(58) Field of Classification Search
CPC ............................ A61K 31/505; C07D 239/47
See application file for complete search history.

(56) References Cited

U.S. PATENT DOCUMENTS

| | | | |
|---|---|---|---|
| 2008/0139534 A1 | 6/2008 | Huang et al. | |
| 2019/0076435 A1 | 3/2019 | Masjedizadeh et al. | |
| 2023/0265056 A1 | 8/2023 | Lu et al. | |

FOREIGN PATENT DOCUMENTS

| | | | |
|---|---|---|---|
| WO | 2006040649 A1 | | 4/2006 |
| WO | 2013184572 A1 | | 12/2013 |
| WO | 2015/79417 A1 | | 6/2015 |
| WO | WO 2015/079417 | * | 6/2015 |
| WO | 2017118277 A1 | | 7/2017 |
| WO | 2020234779 A1 | | 11/2020 |

OTHER PUBLICATIONS

Braga, et al., Crystal Polymorphism and Multiple Crystal Forms, Struct Bond, 132, 25-50, Feb. 25, 2009.
Hilfiker, et al., Relevance of Solid-state Properties for Pharmaceutical Products, Polymorphism: in the Pharmaceutical Industry, Chapter I, 1-19, 2006.
Bernstein, Polymorphism of Molecular Crystals, chapter 7.3.2, 324-330, 2007.
Kummerer, Pharmaceuticals in the environment, Annual Review of Environment and Resources, 35, 57-75, Aug. 18, 2010.
Rodrigez-Spong, et al., General principles of pharmaceutical solid polymorphism: a supramolecular perspective, Advanced Drug Delivery Reviews, 56, 241-274, 2004.
Sarma, et al., Solid forms of pharmaceuticals: Polymorphs, salts and cocrystals, Korean J. Chem. Eng., 28(2), 315-322, Feb. 2011.
Variankaval, et al., From form to function: Crystallization of active pharmaceutical ingredients, AIChE Journal, 54(7), 1682-1688, Jul. 2008.
Hirayama, Handbook of Organic Compound Crystal Preparation-Principle and know-how, chapter 4, p. 57-84, 2008.
Aaltonen, et al., Solid form screening—A review, European Journal of Pharmaceutics and Biopharmaceutics, 71(1), 23-37, 2009.
Hill, et al., Researches on Amines. VIII. Preparation of amino-acetanilide, Journal of the American Chemical Society, 42(8), 1704-1711, 1920.
Kubicova, et al., Synthesis of N, N'-Diarylalkanediamides and Their Antimycobacterial and Antialgal Activity, Molecules, 5, 714-726, 2000.
Reichardt, Solvents and environmental effects in organic chemistry, 611-614, 1991.
Augsburger, et al., Approaches for Improving Bioavailability of Poorly Soluble Drugs—Salt formation, Pharmaceutical Dosage Forms: Tablets, 3rd Edition, vol. 2, 62-66, 2008.
Balbach, et al., Pharmaceutical evaluation of early development candidates, International Journal of Pharmaceutics, 275(1-2), 1-12, May 4, 2004.
Guillory, Generations of Polymorphs, Hydrates, Solvates, and Amorphous Solids, Polymorphism in Pharmaceutical Solids, ed. Brittain, 51 pages, 1999, Marcel Dekker, New York.
Singhal, et al., Drug polymorphism and dosage form design: a practical perspective, Advanced Drug Delivery Reviews, 56(3), 335-347, Feb. 23, 2004.
Zhao, et al., New Technologies in Modern Traditional Chinese Medicine Formulations, Chemical Stability of Drugs, 2007, 363.
Caira M., "Crystalline Polymorphism of Organic Compounds", Topics in Current Chemistry, vol. 198, pp. 163-208, (1998).
Byrn S., "Pharmaceutical Solids: A Strategic Approach to Regulatory Considerations", Pharmaceutical Research, vol. 12(7), pp. 945-954, (1995).

* cited by examiner

*Primary Examiner* — Marcos L Sznaidman
(74) *Attorney, Agent, or Firm* — Francine F. Li

(57) ABSTRACT

This application relates to various anhydrous crystalline forms N-(3-(6-Amino-5-(2-(N-methylacrylamido)ethoxy)pyrimidin-4-yl)-5-fluoro-2-methylphenyl)-4-cyclopropyl-2-fluorobenzamide, as well as compositions, method of making and methods of using the same. These crystalline forms are useful in the treatment of diseases and disorders which are typically ameliorated by the inhibition of BTK. Such diseases and disorders may include inflammatory and autoimmune disorders and pulmonary and respiratory tract inflammation.

45 Claims, 9 Drawing Sheets

CRYSTALLINE FORMS OF A BTK INHIBITOR

CROSS-REFERENCE TO RELATED APPLICATIONS

This application is a 371 U.S. National Phase application of International application number PCT/IB2020/054752 filed 20 May 2020, which claims the benefit of U.S. provisional application Ser. No. 62/851,986 filed 23 May 2019; each of which is incorporated by reference herein in its entirety.

FIELD OF INVENTION

The present disclosure relates to crystalline forms of N-(3-(6-Amino-5-(2-(N-methylacrylamido)ethoxy)pyrimidin-4-yl)-5-fluoro-2-methylphenyl)-4-cyclopropyl-2-fluorobenzamide. The present disclosure also relates to a pharmaceutical composition comprising the crystalline forms, as well as methods for obtaining such crystalline forms and methods of using such crystalline forms in the treatment of diseases and disorders which are typically ameliorated by the inhibition of Bruton's tyrosine kinase. Such diseases and disorders may include inflammatory and autoimmune disorders and pulmonary and respiratory tract inflammation.

BACKGROUND

Polymorphism denotes the existence of more than one crystalline form of a substance.

Solid state form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability.

Therefore, this ability of a chemical substance to crystallize in more than one crystalline form can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown crystalline form during manufacture can have a significant impact.

It is not yet possible to predict whether a particular compound or salt of a compound will form polymorphs, whether any such polymorphs will be suitable for commercial use in a therapeutic composition, or which polymorphs will display such desirable properties. However, understanding which crystalline forms of a drug are possible in certain cases allows researchers to maximize the desired properties of a compound, such as solubility, formulation properties, processing properties, and shelf life. Understanding these factors early in the development of a new drug may mean a more active, more stable, or more cheaply manufactured drug.

Therefore, there is a need to provide a solid state form of N-(3-(6-Amino-5-(2-(N-methylacrylamido)ethoxy)pyrimidin-4-yl)-5-fluoro-2-methylphenyl)-4-cyclopropyl-2-fluorobenzamide, which possesses physicochemical properties allowing for a reliable production of a safe and efficacious drug product comprising N-(3-(6-Amino-5-(2-(N-methylacrylamido)ethoxy)pyrimidin-4-yl)-5-fluoro-2-methylphenyl)-4-cyclopropyl-2-fluorobenzamide.

N-(3-(6-Amino-5-(2-(N-methylacrylamido)ethoxy)pyrimidin-4-yl)-5-fluoro-2-methylphenyl)-4-cyclopropyl-2-fluorobenzamide was first disclosed in WO2015/079417, filed Nov. 28, 2014 in example 6, which is incorporated by reference in its entirety. N-(3-(6-Amino-5-(2-(N-methylacrylamido)ethoxy)pyrimidin-4-yl)-5-fluoro-2-methylphenyl)-4-cyclopropyl-2-fluorobenzamide is a Bruton's tyrosine kinase (BTK) inhibitor having the structure of Formula (I):

Formula (I)

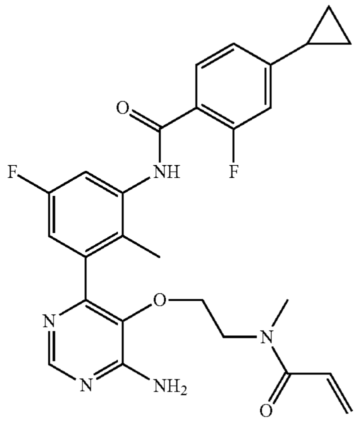

WO2015/079417, however, provides no information about crystalline forms of N-(3-(6-Amino-5-(2-(N-methylacrylamido)ethoxy)pyrimidin-4-yl)-5-fluoro-2-methylphenyl)-4-cyclopropyl-2-fluorobenzamide. Crystalline forms of N-(3-(6-Amino-5-(2-(N-methylacrylamido)ethoxy)pyrimidin- 4-yl)-5-fluoro-2-methylphenyl)-4-cyclopropyl-2-fluorobenzamide have been discovered, which are useful in treating diseases which are typically ameliorated by inhibition of BTK. Such diseases and conditions include inflammatory and autoimmune disorders and pulmonary and respiratory tract inflammation.

SUMMARY

In one aspect, the present invention provides three crystalline forms of N-(3-(6-Amino-5-(2-(N-methylacrylamido)ethoxy)pyrimidin-4-yl)-5-fluoro-2-methylphenyl)-4-cyclopropyl-2-fluorobenzamide in a free form (i.e. a non-salt form). In a particular embodiment, the free forms are anhydrous form of compound of Formula (I).

Embodiments of these crystalline forms include those forms designated herein as Form A, Form B and Form C. The names used herein to identify a specific form, e.g. "Form A" or "Form B" or "Form C", should not be considered limiting with respect to any other substance possessing similar or identical physical and chemical characteristics, but rather it should be understood that these designations are mere identifiers that should be interpreted according to the characterization information also presented herein.

In one aspect, the present invention also provides a pharmaceutical composition comprising: (a) a therapeutically effective amount of crystalline form A of N-(3-(6-Amino-5-(2-(N-methylacrylamido)ethoxy)pyrimidin-4-yl)-5-fluoro-2-methylphenyl)-4-cyclopropyl-2-fluorobenzamide; and (b) at least one pharmaceutically acceptable carrier. Preferably, crystalline Form A is substantially pure. More preferably, Form A is substantially phase pure.

In one aspect, the present invention also provides a pharmaceutical composition comprising: (a) a therapeutically effective amount of a crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide; and (b) at least one pharmaceutically acceptable carrier. Preferably, crystalline Form B is substantially pure. More preferably, Form B is substantially phase pure.

In one aspect, the present invention also provides a process for making crystalline Form A of N-(3-(6-Amino-5-(2-(N-methylacrylamido)ethoxy)pyrimidin-4-yl)-5-fluoro-2-methylphenyl)-4-cyclopropyl-2-fluorobenzamide which comprises the step of:

a) Reacting N-(3-(6-amino-5-(2-(methylamino)ethoxy)pyrimidin-4-yl)-5-fluoro-2-methylphenyl)-4-cyclopropyl-2-fluorobenzamide with acrylic anhydride in a non-chlorinated solvent, optionally in the presence of an inorganic base; and b) Isolating crystalline Form A as a solid (by e.g. anti-solvent crystallization, cooling crystallization, distillation procedure or evaporation of solvent).

In one aspect, the present invention also provides a method for the treatment of disorders mediated by BTK or ameliorated by the inhibition of BTK, comprising administering to a patient in need of such treatment a therapeutically effective amount of crystalline Form A of N-(3-(6-Amino-5-(2-(N-methylacrylamido)ethoxy)pyrimidin-4-yl)-5-fluoro-2-methylphenyl)-4-cyclopropyl-2-fluorobenzamide. Preferably, crystalline Form A is substantially phase pure.

In one aspect, the present invention also provides a method for the treatment of disorders mediated by BTK or ameliorated by the inhibition of BTK, comprising administering to a patient in need of such treatment an effective amount of a substantially phase pure crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide. Preferably, crystalline Form B is substantially phase pure.

In one aspect, the present invention also provides the use of crystalline Form A of N-(3-(6-Amino-5-(2-(N-methylacrylamido)ethoxy)pyrimidin-4-yl)-5-fluoro-2-methylphenyl)-4-cyclopropyl-2-fluorobenzamide for the preparation of a medicament for the treatment of disorders mediated by BTK or ameliorated by the inhibition of BTK. Preferably, crystalline Form A is substantially phase pure.

In one aspect, the present invention also provides the use of a substantially phase pure crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide for the preparation of a medicament for the treatment of disorders mediated by BTK or ameliorated by the inhibition of BTK. Preferably, crystalline Form B is substantially phase pure.

In one aspect, the present invention also provides crystalline Form A of N-(3-(6-Amino-5-(2-(N-methylacrylamido)ethoxy)pyrimidin-4-yl)-5-fluoro-2-methylphenyl)-4-cyclopropyl-2-fluorobenzamide for use in the treatment of disorders mediated by BTK or ameliorated by the inhibition of BTK. Preferably, crystalline Form A is substantially phase pure.

In one aspect, the present invention also provides a substantially phase pure crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide for use in the treatment of disorders mediated by BTK or ameliorated by the inhibition of BTK. Preferably, crystalline Form B is substantially phase pure.

Accordingly, crystalline forms of compound of Formula (I) as described herein are useful in the treatment of the following diseases or disorders mediated by BTK or ameliorated by inhibition of BTK: Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic urticaria (chronic spontaneous urticaria, inducible urticaria), chronic allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including, but not limited to, multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

Crystalline forms of the compound of Formula (I) are especially useful in the treatment of rheumatoid arthritis; chronic urticaria, preferably chronic spontaneous urticaria; Sjögren's syndrome, multiple sclerosis, atopic dermatitis or asthma.

Figure 1:
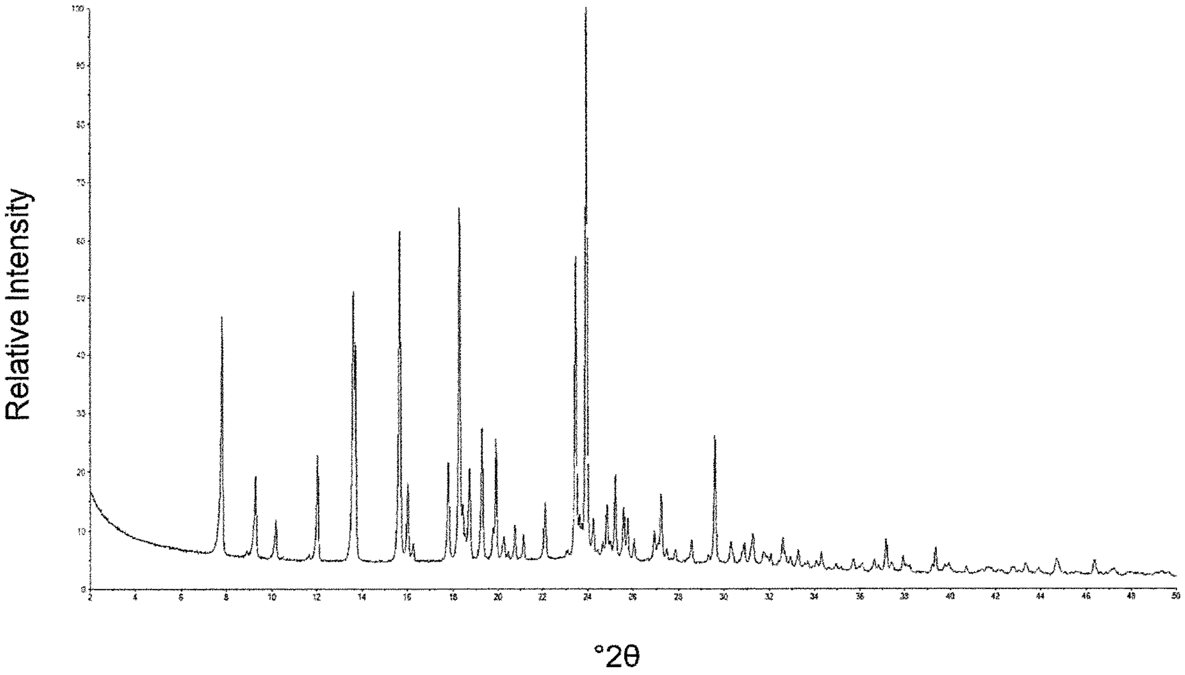
FIG. 1 provides an illustrative XRPD spectrum for an anhydrous crystalline form of compound of Formula (I), designated herein as Form A, showing degrees 2θ (2-theta) on the X-axis and relative intensity on the Y-axis.

More detailed listings of the XRPD peaks for each of forms A, B and C are set forth in Tables 1 and 2, respectively below, in which the % relative intensity ($I/I_0 \times 100$) is also provided. It should be understood that in the X-ray powder diffraction spectra or pattern that there is inherent variability in the values measured in degrees 2θ (° 2θ) as a result of, for example, instrumental variation (including differences between instruments). As such, it should be understood that there is a variability of up to ±0.2 °2θ in XRPD peak measurements and yet such peak values would still be considered to be representative of a particular solid state form of the crystalline materials described herein. It should also be understood that other measured values from XRPD experiments and DSC/TGA experiments, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE DISCLOSURE

Definition

As used herein, the terms "about" and "substantially" indicate with respect to features such as endotherms, endothermic peak, exotherms, baseline shifts, etc., that their values can vary. With reference to X-ray diffraction peak positions, "about" or "substantially" means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only. For DSC, variation in the temperatures observed will depend upon the rate of temperature change as well as sample preparation technique and the particular instrument employed. Thus, the endotherm/melting point values reported herein relating to DSC/TGA thermograms can vary ±5° C. (and still be considered to be characteristic of the particular crystalline form described herein). When used in the context of other features, such as, for example, percent by weight (% by weight), reaction temperatures, the term "about" indicates a variance of ±5%.

The terms "crystalline form(s)" or "crystalline modification(s)" or "polymorphic form(s)" or "polymorph(s)" will be used interchangeably herein. As used herein "polymorph" refers to crystalline forms having the same chemical composition but different spatial arrangements of the molecules, atoms, and/or ions forming the crystal. Each polymorph differ with respect to thermodynamic stability, physical parameters, x-ray structure and methods of preparation.

As used herein "amorphous" refers to a solid form of a molecule, atom, and/or ions that is not crystalline. An amorphous solid does not display a definitive X-ray diffraction pattern.

As used herein, "substantially pure," when used in reference to a form, means a compound having a purity greater than 90 weight %, including greater than 90, 91, 92, 93, 94, 95, 96, 97, 98, and 99 weight %, and also including equal to about 100 weight % of Compound of Formula (I), based on the weight of the compound. The remaining material comprises other form(s) of the compound, and/or reaction impurities and/or processing impurities arising from its preparation. For example, a crystalline form of Compound of Formula (I) may be deemed substantially pure in that it has a purity greater than 90 weight %, as measured by means that are at this time known and generally accepted in the art, where the remaining less than 10 weight % of material comprises other form(s) of Compound of Formula (I) and/or reaction impurities and/or processing impurities.

As used herein, "substantially phase pure," when used in reference to any crystalline form of the compound of Formula (I), means a compound having a phase purity of greater than about 90% by weight, including greater than about 90, 91, 92, 93, 94, 95, 96, 97, 98, and about 99% by weight, and also including equal to about 100% by weight of the compound of Formula (I), based on the weight of the compound on an anhydrous basis. The term "phase pure" or "phase purity" herein refers to phase homogeneity with respect to a particular solid state form of the compound of Formula (I) and does not necessarily imply a high degree of chemical purity absent an express statement to that effect. Phase purity may be determined according to methods known in the art, for example, using XRPD to do quantitative phase analysis using one or more approaches known in the art, for example, via an external standard method, direct comparisons of line (peak) characteristics which are attributed to different phases in a particular spectra, or via an internal standard method. However XRPD quantification of phase purity can be complicated by the presence of amorphous material. Accordingly, other methods that may be useful for determining phase purity include, for example, solid state NMR spectroscopy, Raman and/or infrared spectroscopy. One of skilled in the art would readily understand these methods and how to employ these additional (or alternative) methods for determining phase purity.

As used herein, "substantially chemically pure" when used in reference to any crystalline form of the compound of Formula (I), means a compound having a chemical purity greater than about 90% by weight, including greater than about 90, 91, 92, 93, 94, 95, 96, 97, 98, and about 99% by weight, and also including equal to about 100% by weight of the compound of Formula (I), based on the weight of the compound on an anhydrous basis. The remaining material generally comprises other compounds, such as for example, other stereoisomers of the compound of Formula (I), reaction impurities, starting materials, reagents, side products, and/or other processing impurities arising from the preparation and/or isolation and/or purification of the particular crystalline form. For example, a crystalline form of the compound of Formula (I) may be deemed to be substantially chemically pure if it has been determined to have a chemical purity of greater than about 90% by weight, as measured by standard and generally accepted methods known in the art, where the remaining less than about 10% by weight constitutes other materials such as other stereoisomers of the compound of Formula (I), reaction impurities, starting materials, reagents, side products, and/or processing impurities. Chemical purity may be determined according to methods known in the art, for example, high performance liquid chromatography (HPLC), LC-MS (liquid chromatography—mass spectrometry), nuclear magnetic resonance (NMR) spectroscopy, or infrared spectroscopy. One of skill in the art would readily understand these methods and how to employ these additional (or alternative) methods for determining chemical purity.

As used herein, the term "seed" can be used as a noun to describe one or more crystals of a crystalline compound of Formula (I). The term "seed" can also be used as a verb to describe the act of introducing said one or more crystals of a crystalline compound of Formula (I) into an environment (including, but not limited to e.g., a solution, a mixture, a suspension, or a dispersion) thereby resulting in the formation of more crystals or the growth of the introduced crystals of the crystalline compound of Formula (I).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by BTK, or (ii) associated with BTK activity, or (iii) characterized by activity (normal or abnormal) of BTK; or (2) reducing or inhibiting the activity of BTK; or (3) reducing or inhibiting the expression of BTK. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of BTK; or reducing or inhibiting the expression of BTK partially or completely.

As used herein, the term "subject" refers to an animal. Preferably, the animal is a mammal. A subject refers to for example, primates (e.g. humans), cows, sheep, goats, horses, dogs, cats, rabbits, rats, mice, fish, birds and the like. In a preferred embodiment, the subject is a human.

As used herein, a subject is "in need of" or "in need thereof" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "inhibit", "inhibition" or "inhibiting" refers to the reduction or suppression of a given condition, symptom, or disorder, or disease, or a significant decrease in the baseline activity of a biological activity or process.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In one embodiment, "treat" or "treating" refers to delaying the progression of the disease or disorder.

As used herein, the term "prevent", "preventing" or "prevention" of any disease or disorder refers to the prophylactic treatment of the disease or disorder; or delaying the onset of the disease or disorder.

The term "comprising" encompasses "including" as well as "consisting"; e.g., a composition comprising X may consist exclusively of X or may include additional, e.g. X and Y.

As used herein the term "combination" refers to either a fixed combination in one dosage unit form, or a combined administration where a crystalline form of compound of Formula (I) and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that a crystalline form of the compound of Formula (I) and a combination partner (i.e. immunotherapeutic agent), are both administered to a patient simultaneously in the form of a single entity or dosage. The term "non-fixed combination" means that a crystalline form of the compound of Formula (I) and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat a BTK related disease as described in the present disclosure. Such administration encompasses co-administration of these therapeutic agents in a substantially simultaneous manner, such as in a single capsule having a fixed ratio of active ingredients.

Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Crystalline Forms:

The present disclosure relates to anhydrous crystalline forms of N-(3-(6-Amino-5-(2-(N-methylacrylamido)ethoxy)pyrimidin-4-yl)-5-fluoro-2-methylphenyl)-4-cyclopropyl-2-fluorobenzamide (the compound of Formula (I)), which are described and characterized herein.

In one embodiment, the present disclosure provides a crystalline form of N-(3-(6-Amino- 5-(2-(N-methylacrylamido)ethoxy)pyrimidin-4-yl)-5-fluoro-2-methylphenyl)-4-cyclopropyl-2-fluorobenzamide (Form A) having an X-ray powder diffraction (XRPD) pattern comprising a representative peak, in terms of °2θ, at 23.9±0.2 °2θ measured at a temperature of about 25° C. In another embodiment, the XRPD pattern further comprises one or more additional representative peaks chosen from 15.6±0.2 °2θ, 18.3±0.2 °2θ and 23.4±0.2 °2θ. In one aspect of the previous embodiment, the XRPD pattern further comprises one or more additional representative peaks chosen from 7.8±0.2 °2θ, 13.6±0.2 °2θ, 19.2±0.2 °2θ, 19.9±0.2 °2θ and 29.6±0.2 °2θ measured at a temperature of about 25° C. In one aspect of the previous embodiment, the XRPD pattern for the crystalline Form A of the compound of Formula (I) may further comprise one, two, three, or four representative peaks selected from 9.2±0.2 °2θ, 12.0±0.2 °2θ, 17.8±0.2 °2θ, 18.7±0.2 °2θ, 19.2±0.2 °2θ, 19.9±0.2 °2θ, 25.2±0.2 °2θ, and 29.6±0.2 °2θ measured at a temperature of about 25° C. Thus, the XRPD pattern for the crystalline Form A of the compound of Formula (I) may comprise one or more representative peaks selected from 7.8±0.2 °2θ, 9.2±0.2 °2θ, 12.0±0.2 °2θ, 13.6±0.2 °2θ, 15.6±0.2 °2θ, 16.0±0.2 °2θ, 17.8±0.2 °2θ, 18.3±0.2 °2θ, 18.7±0.2 °2θ, 19.2±0.2 °2θ, 19.9±0.2 °2θ, 22.1±0.2 °2θ, 23.4±0.2 °2θ, 23.9±0.2 °2θ, 24.8±0.2 °2θ, 25.2±0.2 °2θ, 25.5±0.2 °2θ, 27.2±0.2 °2θ, and 29.6±0.2 °2θ, measured at a temperature of about 25° C. The XRPD pattern for the crystalline Form A may comprise one or more (e.g. two, three, four, five or six) representative peaks selected from the peaks disclosed in table 1 and measured at a temperature of about 25° C.

In another aspect of the above embodiment, the crystalline Form A of compound of Formula (I) is characterized by a x-ray powder diffraction pattern comprising four or more 2θ values (CuKα λ=1.54184 Å) selected from the group consisting of 7.8±0.2 °2θ, 9.2±0.2 °2θ, 12.0±0.2 °2θ, 13.6±0.2 °2θ, 15.6±0.2 °2θ, 16.0±0.2 °2θ, 17.8±0.2 °2θ, 18.3±0.2 °2θ, 18.7±0.2 °2θ, 19.2±0.2 °2θ, 19.9±0.2 °2θ, 22.1±0.2 °2θ, 23.4±0.2 °2θ, 23.9±0.2 °2θ, 24.8±0.2 °2θ, 25.2±0.2 °2θ, 25.5±0.2 °2θ, 27.2±0.2 °2θ, and 29.6±0.2 °2θ, measured at a temperature of about 25° C. In another aspect of the above embodiment, the crystalline Form A of compound of Formula (I) is characterized by a x-ray powder diffraction pattern comprising five or more 2θ values (CuKα λ=1.54184 Å) selected from the group consisting of 7.8±0.2 °2θ, 9.2±0.2 °2θ, 12.0±0.2 °2θ, 13.6±0.2 °2θ, 15.6±0.2 °2θ, 16.0±0.2 °2θ, 17.8±0.2 °2θ, 18.3±0.2 °2θ, 18.7±0.2 °2θ, 19.2±0.2 °2θ, 19.9±0.2 °2θ, 22.1±0.2 °2θ, 23.4±0.2 °2θ, 23.9±0.2 °2θ, 24.8±0.2 °2θ, 25.2±0.2 °2θ, 25.5±0.2 °2θ, 27.2±0.2 °2θ, and 29.6±0.2 °2θ measured at a temperature of about 25° C.

In yet another aspect of the above embodiment, the crystalline Form A of the compound of Formula (I) has an XRPD pattern substantially as shown in FIG. 1.

The crystalline Form A of N-(3-(6-Amino-5-(2-(N-methylacrylamido)ethoxy)pyrimidin-4-yl)-5-fluoro-2-methylphenyl)-4-cyclopropyl-2-fluorobenzamide may be characterized thermally. In one embodiment, crystalline Form A of the compound of Formula (I) has a thermal profile measured by Differential Scanning Calorimetry (DSC) with a heating rate of 10° C./min comprising a single endothermic peak starting at about 194° C. (corresponding to melting).

Figure 2:
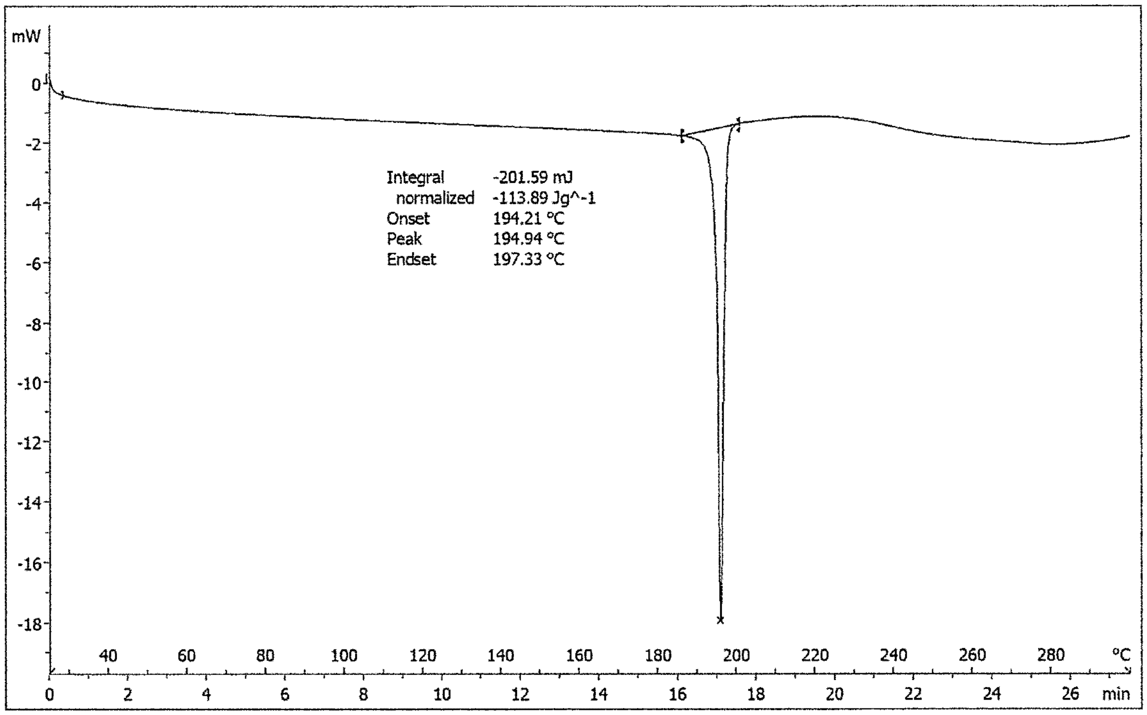
FIG. 2 provides an illustrative DSC for an anhydrous crystalline form of the compound of Formula (I), designated herein as Form A.

In another embodiment, the crystalline Form A of the compound of Formula (I) has a DSC thermogram that is substantially as shown in FIG. 2. It should be understood that hydrated forms may yield different thermograms (in terms of peak shape and profile) depending on instrument parameters, thus the same material may have thermograms that look substantially different from each other when the data is generated on two different instruments.

Figure 3:
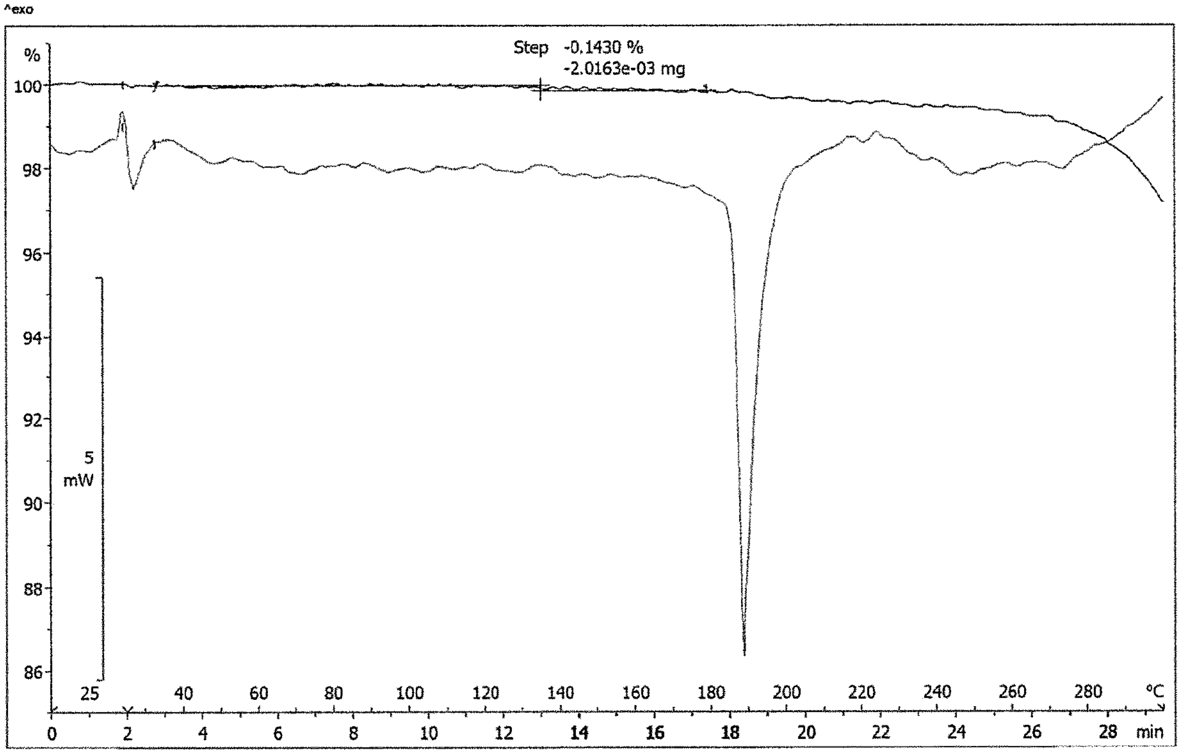
FIG. 3 provides an illustrative TGA for an anhydrous crystalline form of the compound of Formula (I), designated herein as Form A.

In another embodiment, the crystalline Form A of the compound of Formula (I) has a thermogravimetric analysis (TGA) diagram substantially the same as that shown in shown in FIG. 3. The weight loss by TGA is about 0.3% in the range of 40-200° C. Thermal decomposition occurred at 240° C.

In yet another embodiment, the crystalline Form A is substantially pure.

In yet another embodiment, the crystalline Form A is substantially chemically pure.

In yet another embodiment, the crystalline Form A is substantially phase pure.

In one embodiment, the invention pertains to a process for making crystalline Form A of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

a) Reacting N-(3-(6-amino-5-(2-(methylamino)ethoxy)pyrimidin-4-yl)-5-fluoro-2-methylphenyl)-4-cyclopropyl-2-fluorobenzamide with acrylic anhydride in a non-chlorinated solvent, optionally in the presence of an inorganic base; and
b) Isolating crystalline Form A as a solid (by e.g. anti-solvent crystallization, cooling crystallization, distillation procedure or evaporation of solvent).

In another embodiment, the invention pertains to a process for making crystalline Form A of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

(a) Reacting N-(3-(6-amino-5-(2-(methylamino)ethoxy)pyrimidin-4-yl)-5-fluoro-2-methylphenyl)-4-cyclopropyl-2-fluorobenzamide with acrylic anhydride in a non-chlorinated solvent, optionally in the presence of a base;
(b) Adding water to quench the reaction forming an aqueous and an organic phase;
(c) Separating the organic phase;
(d) washing the organic phase with an acidic solution; and
(e) Isolating crystalline Form A as a solid (by e.g. anti-solvent crystallization, cooling crystallization, distillation procedure or evaporation of solvent).

In one aspect of the previous two embodiments, step (a) of the process is carried out at temperature of about 20° C. to about 65° C. Preferably, step (a) is carried at temperatures of about 40° C. to about 65° C., most preferably at a temperature of about 50° C.

In yet another aspect of the previous three embodiments, step (a) of said process is carried out in a non-chlorinated solvent selected from ethyl acetate and isopropyl acetate, preferably ethyl acetate.

In yet another aspect of the previous four embodiments, step (a) is carried out in the presence of an inorganic base, preferably a carbonate base, more preferably sodium carbonate.

In another aspect of the previous five embodiments, the process further comprises a step after step (b) but before step (c) which consists of stirring and heating the reaction mixture to temperatures of about 50° C. to about 65° C. and cooling to room temperature prior to step (c). This additional step may be useful to more efficiently remove the acrylic acid by-product.

In another aspect of previous six embodiment, the acidic solution used in step (d) has a pH of about 1. For example, the acid solution is a sulfuric acid solution (e.g. 0.05M). The organic phase is washed with an acidic solution in order to remove the following side product from the reaction mixture:

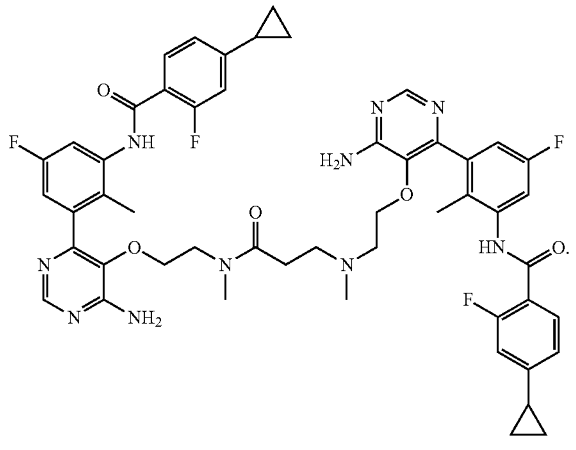 [SMILES: Cc1c(NC(=O)c2ccc(C3CC3)cc2F)cc(F)cc1-c1ncnc(N)c1OCCN(C)CCC(=O)N(C)CCOc1c(N)ncnc1-c1cc(F)cc(NC(=O)c2ccc(C3CC3)cc2F)c1C]

In yet another aspect of the previous seven embodiments, Form A is isolated as a solid by anti-solvent crystallization. An anti-solvent is a solvent in which compound of Formula (I) has low solubility (e.g. a solubility of less than 0.5 mg/mL, preferably less than 0.25 mg/mL). Non-limiting examples of anti-solvents for use in the process are heptane, hexane, t-butyl methyl ether, toluene or acetonitrile.

In yet a preferred aspect of the previous seven embodiments, Form A is isolated as a solid by distillation procedure.

The present invention also provides a process for making Form A of N-(3-(6-Amino-5-(2-(N-methylacrylamido)ethoxy)pyrimidin-4-yl)-5-fluoro-2-methylphenyl)-4-cyclopropyl-2-fluorobenzamide which comprises the step of:
(a) suspending a crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide, or a crystalline form C of N-(3-(6-Amino-5-(2-(N-methylacrylamido)ethoxy)pyrimidin-4-yl)-5-fluoro-2-methylphenyl)-4-cyclopropyl-2-fluorobenzamide; or mixture of Form B and Form C, in a non-chlorinated solvent; and
(b) and isolating Form A as a solid (by e.g. anti-solvent crystallization, cooling crystallization, distillation procedure or evaporation of solvent)

The present invention also provides a process for making Form A of N-(3-(6-Amino-5-(2-(N-methylacrylamido)ethoxy)pyrimidin-4-yl)-5-fluoro-2-methylphenyl)-4-cyclopropyl-2-fluorobenzamide which comprises the step of:
(a) suspending a crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide, or a crystalline form C of N-(3-(6-Amino-5-(2-(N-methylacrylamido)ethoxy)pyrimidin- 4-yl)-5-fluoro-2-methylphenyl)-4-cyclopropyl-2-fluorobenzamide; or mixture of Form B and Form C, in a non-chlorinated solvent; and
(b) letting the suspension equilibrate at room temperature for at least 2 weeks, or letting the suspension equilibrate at 50° C. for at least one week; and
(c) isolating Form A as a solid (by e.g. anti-solvent crystallization, cooling crystallization, distillation procedure or evaporation of solvent)

In one aspect of the previous 2 embodiments, the non-chlorinated solvent is selected from 1,4-dioxane, alcohol, acetone, acetonitrile, tetrahydrofuran, water, pyridine, nitromethane, anisole, alkyl acetate.

In yet another aspect of the previous three embodiments, crystalline Form B, or crystalline Form C, or mixture thereof, may dissolved depending on the non-chlorinated solvent. In such case, isolating Form A as a solid may involves anti-solvent crystallization, cooling crystallization, distillation procedure or evaporation of solvent. In other aspect, Form B, Form C, or mixture thereof may remain in suspension, in which case, Form A is isolating by filtration.

The present invention further provides a crystalline form of a N-(3-(6-Amino-5-(2-(N-methylacrylamido)ethoxy)pyrimidin-4-yl)-5-fluoro-2-methylphenyl)-4-cyclopropyl-2-fluorobenzamide (Form B) having an X-ray powder diffraction (XRPD) pattern comprising a representative peak, in terms of °2θ, at 20.9±0.2 °2θ, measured at a temperature of about 25° C. In another embodiment, the XRPD pattern further comprises one or more additional representative peaks chosen from 6.7±0.2 °2θ, 11.1±0.2 °2θ, 17.9±0.2 °2θ, 20.2±0.2 °2θ, 20.9±0.2 °2θ and 24.0±0.2 °2θ, measured at a temperature of about 25° C. In one aspect of the previous embodiment, the XRPD pattern for the crystalline Form B may further comprise one, two, three, or four representative peaks chosen from 5.9±0.2 °2θ, 13.0±0.2 °2θ, 14.8±0.2 °2θ, 19.0±0.2 °2θ and 22.6±0.2 °2θ, measured at a temperature of about 25° C.

Thus, the XRPD pattern for the crystalline Form B may comprise one or more (e.g. two, three, four, five or six) representative peaks chosen from 5.9±0.2 °2θ, 6.7±0.2 °2θ, 7.8±0.2 °2θ, 8.3±0.2 °2θ, 11.1±0.2 °2θ, 12.1±0.2 °2θ, 12.6±0.2 °2θ, 13.0±0.2 °2θ, 13.3±0.2 °2θ, 14.8±0.2 °2θ, 15.8±0.2 °2θ, 16.4±0.2 °2θ, 17.6±0.2 °2θ, 19.5±0.2 °2θ, 20.2±0.2 °2θ, 20.6±0.2 °2θ, 20.9±0.2 °2θ, 21.6±0.2 °2θ, 22.3±0.2 °2θ, 23.3±0.2 °2θ, 24.0±0.2 °2θ, 24.9±0.2 °2θ and 25.3±0.2 °2θ. The XRPD pattern for the crystalline Form B may comprise one or more (e.g. two, three, four, five or six) representative peaks selected from the peaks disclosed in table 2 and measured at a temperature of about 25° C. chosen from peaks disclosed in table 2.

In another embodiment, said Form B is characterized by a x-ray powder diffraction pattern comprising four or more 2θ values (CuKα λ=1.54184 Å) selected from the group consisting of 5.9±0.2 °2θ, 6.7±0.2 °2θ, 7.8±0.2 °2θ, 8.3±0.2 °2θ, 11.1±0.2 °2θ, 12.1±0.2 °2θ, 12.6±0.2 °2θ, 13.0±0.2 °2θ, 13.3±0.2 °2θ, 14.8±0.2 °2θ, 15.8±0.2 °2θ, 16.4±0.2 °2θ, 17.6±0.2 °2θ, 19.5±0.2 °2θ, 20.2±0.2 °2θ, 20.6±0.2 °2θ, 20.9±0.2 °2θ, 21.6±0.2 °2θ, 22.3±0.2 °2θ, 23.3±0.2 °2θ, 24.0±0.2 °2θ, 24.9±0.2 °2θ and 25.3±0.2 °2θ measured at a temperature of about 25° C.

In another embodiment, said Form B is characterized by a x-ray powder diffraction pattern comprising five or more 2θ values (CuKα λ=1.54184 Å) selected from the group consisting of 5.9±0.2 °2θ 67 0.2 °2θ, 7.8±0.2 °2θ, 8.3±0.2 °2θ, 11.1±0.2 °2θ, 12.1±0.2 °2θ, 12.6±0.2 °2θ, 13.0±0.2 °2θ, 13.3±0.2 °2θ, 14.8±0.2 °2θ, 15.8±0.2 °2θ, 16.4±0.2 °2θ, 17.6±0.2 °2θ, 19.5±0.2 °2θ, 20.2±0.2 °2θ, 20.6±0.2 °2θ, 20.9±0.2 °2θ, 21.6±0.2 °2θ, 22.3±0.2 °2θ, 23.3±0.2 °2θ, 24.0±0.2 °2θ, 24.9±0.2 °2θ and 25.3±0.2 °2θ measured at a temperature of about 25° C.

Figure 4:
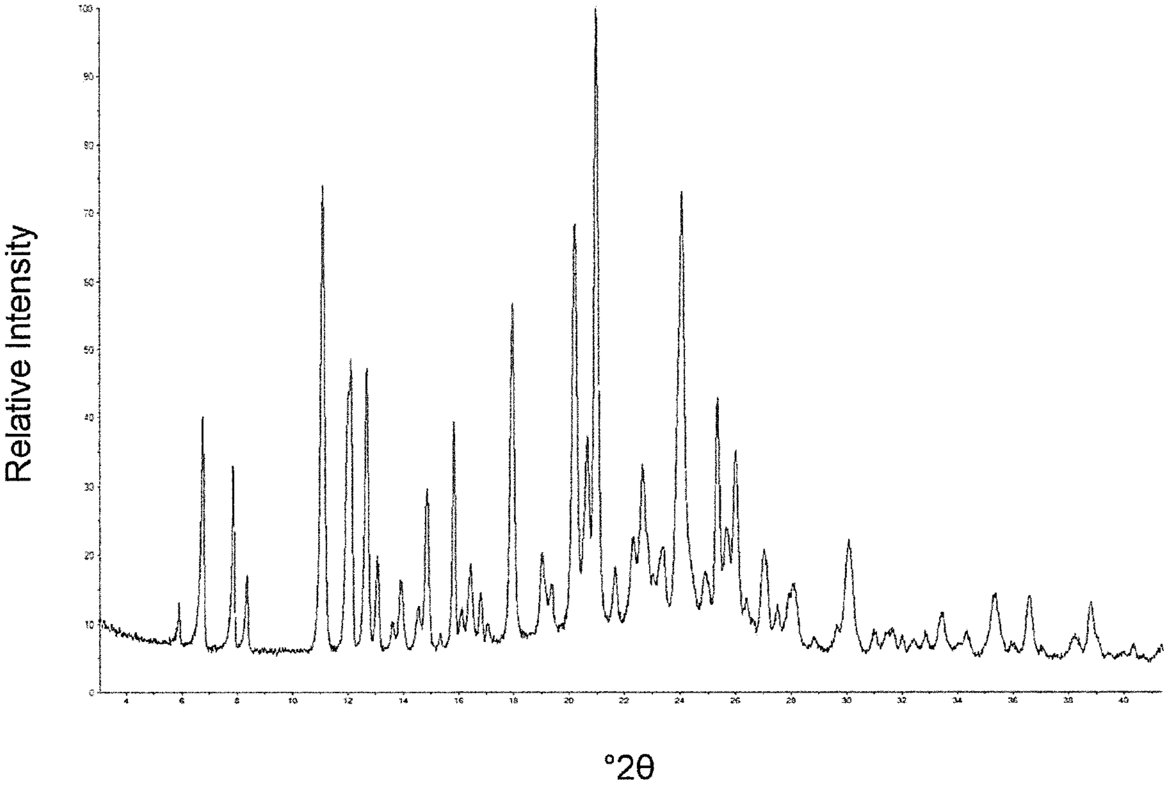
FIG. 4 provides an illustrative XRPD spectrum for an anhydrous crystalline form of compound of Formula (I), designated herein as Form B, showing degrees 2θ (2-theta) on the X-axis and relative intensity on the Y-axis.

In yet another embodiment, crystalline Form B of the compound of Formula (I) has a XRPD pattern substantially as shown in FIG. 4.

The crystalline Form B of N-(3-(6-Amino-5-(2-(N-methylacrylamido)ethoxy)pyrimidin-4-yl)-5-fluoro-2-methylphenyl)-4-cyclopropyl-2-fluorobenzamide may be characterized thermally. In one embodiment, crystalline Form B of the compound of Formula (I) has a differential thermogravimetric profile measured by DSC with a heating rate of 10° C./min, comprising an endothermic peak starting at about 170° C. (corresponding to the melting of Modification B) and an exothermic peak starting at about 175° C. (corresponding to the recrystallization into Modification A) and an endothermic peak starting at about 194° C. (corresponding to the melting of modification A).

Figure 5:
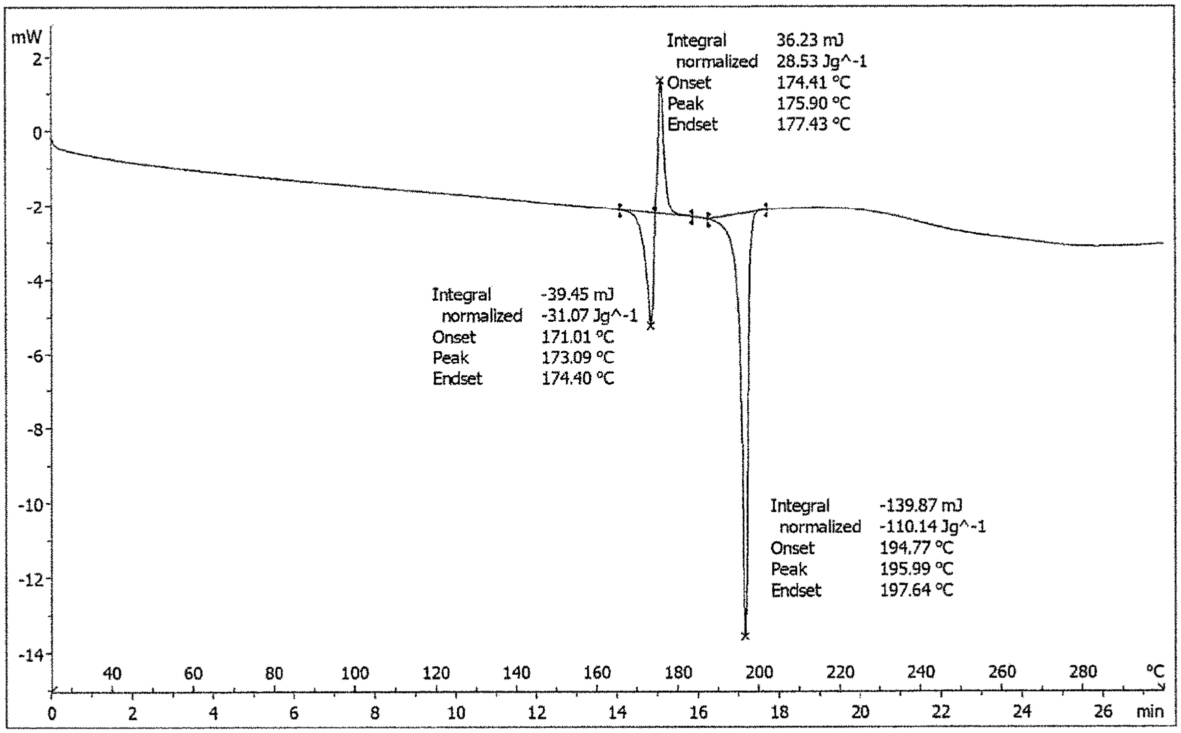
FIG. 5 provides an illustrative DSC for an anhydrous crystalline form of the compound of Formula (I), designated herein as Form B.

In another embodiment, crystalline Form B of the compound of Formula (I) has a DSC thermogram that is substantially as shown in FIG. 5. It should be understood that hydrated forms may yield different thermograms (in terms of peak shape and profile) depending on instrument parameters, thus the same material may have thermograms that look substantially different from each other when the data is generated on two different instruments In another embodiment, crystalline Form B of the compound of Formula (I) has a thermogravimetric analysis (TGA) diagram substantially the same as that shown in shown in FIG. 6. The weight loss by TGA is about 0.2% in the range of 40-160° C. Thermal decomposition occurred above 240° C.

In yet another embodiment, the crystalline Form B is substantially pure.

In yet another embodiment, the crystalline Form B is substantially chemically pure.

In yet another embodiment, the crystalline Form B is substantially phase pure.

In one embodiment, the invention pertains to a process for making crystalline Form B of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

(a) Suspending Form A in dichloromethane at a temperature of about 40° C. for about 3 days;
(b) Letting the suspension equilibrate a room temperature for about 5 days; and
(c) Isolating Form B as a solid (e.g. by filtration).

In yet another embodiment, the invention pertains to a process for making crystalline Form B of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

a) Suspending Modification A in a solvent mixture comprising at least 50% by volume of dichloromethane;
b) Letting the suspension equilibrate at a temperature of about 50° C. for about 2 weeks;
c) Cooling down the suspension to room temperature; and
d) Isolating the solid from the suspension (e.g. by filtration).

In one aspect of the above embodiment, the solvent mixture is MeOH/dichloromethane 50:50 (v/v).

The present invention further provides a crystalline form of a N-(3-(6-Amino-5-(2-(N-methylacrylamido)ethoxy)pyrimidin-4-yl)-5-fluoro-2-methylphenyl)-4-cyclopropyl-2-fluorobenzamide (Form C) having an X-ray powder diffraction (XRPD) pattern comprising a representative peak, in terms of °2θ, at 5.9±0.2 °2θ, measured at a temperature of about 25° C. In another embodiment, the XRPD pattern further comprises one or more additional representative peaks chosen from 11.9±0.2 °2θ, 17.0±0.2 °2θ, and 19.3±0.2 °2θ, measured at a temperature of about 25° C. In one aspect of the previous embodiment, the XRPD pattern for the crystalline Form C may further comprise one, two, three, or four representative peaks chosen from 12.5±0.2 °2θ, 15.3±0.2 °2θ, 18.0±0.2 °2θ, 21.0±0.2 °2θ, 21.2±0.2 °2θ, 23.4±0.2 °2θ, and 23.7±0.2 °2θ, measured at a temperature of about 25° C.

Thus, the XRPD pattern for the crystalline Form C may comprise one or more (e.g. two, three, four, five or six) representative peaks chosen from 5.9±0.2 °2θ, 11.9±0.2 °2θ, 12.0±0.2 °2θ, 12.5±0.2 °2θ, 12.9±0.2 °2θ, 14.4±0.2 °2θ, 14.6±0.2 °2θ, 15.3±0.2 °2θ, 17.0±0.2 °2θ, 18.0±0.2 °2θ, 19.0±0.2 °2θ, 19.2±0.2 °2θ, 19.9±0.2 °2θ, 20.2±0.2 °2θ, 20.8±0.2 °2θ, 21.0±0.2 °2θ, 21.2±0.2 °2θ, 22.8±0.2 °2θ, 23.4±0.2 °2θ, 23.7±0.2 °2θ, 25.3±0.2 °2θ, 26.1±0.2 °2θ and 26.9±0.2 °2θ. The XRPD pattern for the crystalline Form C may comprise one or more (e.g. two, three, four, five or six) representative peaks selected from the peaks disclosed in table 3 and measured at a temperature of about 25° C. chosen from peaks disclosed in table 3.

In another embodiment, said Form C is characterized by a x-ray powder diffraction pattern comprising four or more 2θ values (CuKα λ=1.54184 Å) selected from the group consisting of 5.9±0.2 °2θ, 11.9±0.2 °2θ, 12.0±0.2 °2θ, 12.5±0.2 °2θ, 12.9±0.2 °2θ, 14.4±0.2 °2θ, 14.6±0.2 °2θ, 15.3±0.2 °2θ, 17.0±0.2 °2θ, 18.0±0.2 °2θ, 19.0±0.2 °2θ, 19.2±0.2 °2θ, 19.9±0.2 °2θ, 20.2±0.2 °2θ, 20.8±0.2 °2θ, 21.0±0.2 °2θ, 21.2±0.2 °2θ, 22.8±0.2 °2θ, 23.4±0.2 °2θ, 23.7±0.2 °2θ, 25.3±0.2 °2θ, 26.1±0.2 °2θ and 26.9±0.2 °2θ measured at a temperature of about 25° C.

In another embodiment, said Form C is characterized by a x-ray powder diffraction pattern comprising five or more 2θ values (CuKα λ=1.54184 Å) selected from the group consisting of 5.9±0.2 °2θ, 11.9±0.2 °2θ, 12.0±0.2 °2θ, 12.5±0.2 °2θ, 12.9±0.2 °2θ, 14.4±0.2 °2θ, 14.6±0.2 °2θ, 15.3±0.2 °2θ, 17.0±0.2 °2θ, 18.0±0.2 °2θ, 19.0±0.2 °2θ, 19.2±0.2 °2θ, 19.9±0.2 °2θ, 20.2±0.2 °2θ, 20.8±0.2 °2θ, 21.0±0.2 °2θ, 21.2±0.2 °2θ, 22.8±0.2 °2θ, 23.4±0.2 °2θ, 23.7±0.2 °2θ, 25.3±0.2 °2θ, 26.1±0.2 °2θ and 26.9±0.2 °2θ measured at a temperature of about 25° C.

Figure 7:
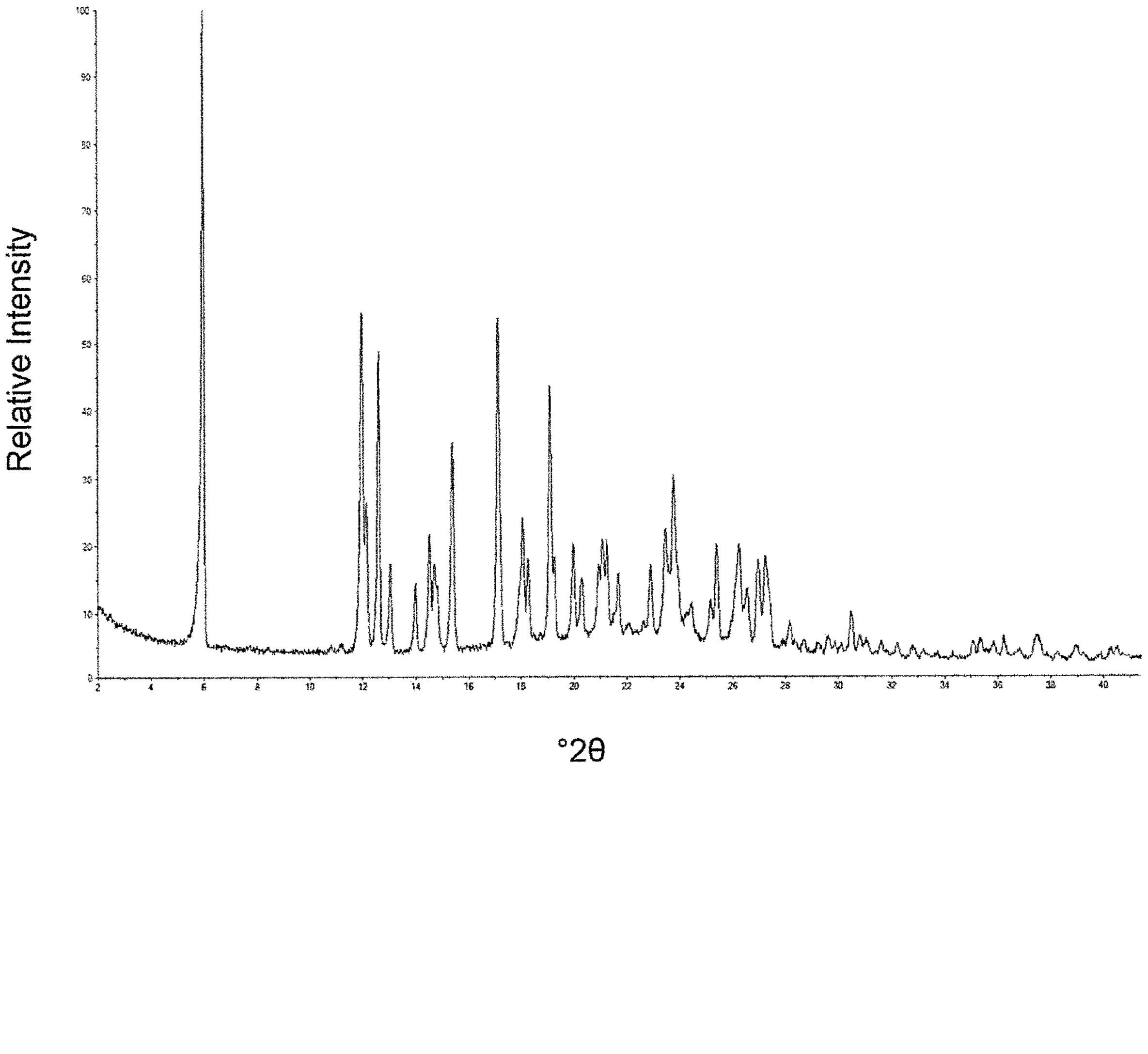
FIG. 7 provides an illustrative XRPD spectrum for an anhydrous crystalline form of compound of Formula (I), designated herein as Form C, showing degrees 2θ (2-theta) on the X-axis and relative intensity on the Y-axis.

In yet another embodiment, crystalline Form C of the compound of Formula (I) has an XRPD pattern substantially as shown in FIG. 7.

The crystalline Form C of N-(3-(6-Amino-5-(2-(N-methylacrylamido)ethoxy)pyrimidin-4-yl)-5-fluoro-2-methylphenyl)-4-cyclopropyl-2-fluorobenzamide may be characterized thermally. In one embodiment, crystalline Form C of the compound of Formula (I) has a differential thermogravimetric profile measured by DSC with a heating rate of 10° C./min, comprising a small exothermic peak between 9° and 120° C. (corresponding to the solid/solid transition from Modification C to Modification B), an endothermic peak starting at about 171° C. (corresponding to the melting of Modification B) and an exothermic peak starting at about 175° C. (corresponding to the recrystallization into Modification A) and an endothermic peak starting at about 195° C. (corresponding to the melting of modification A).

Figure 8:
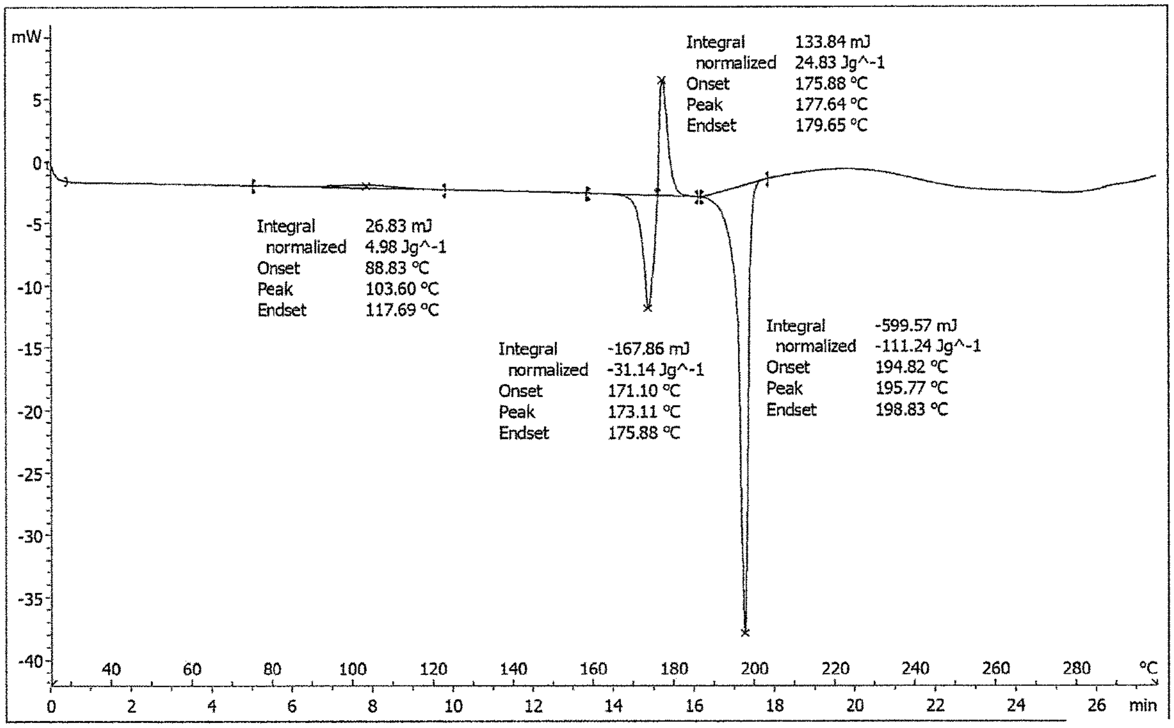
FIG. 8 provides an illustrative DSC for an anhydrous crystalline form of the compound of Formula (I), designated herein as Form C.

In another embodiment, crystalline Form C of the compound of Formula (I) has a DSC thermogram that is substantially as shown in FIG. 8. It should be understood that hydrated forms may yield different thermograms (in terms of peak shape and profile) depending on instrument parameters, thus the same material may have thermograms that look substantially different from each other when the data is generated on two different instruments In another embodiment, a crystalline Form C has a thermogravimetric analysis (TGA) diagram substantially the same as that shown in shown in FIG. 9. The weight loss by TGA is about 0.01% in the range of 40-150° C. Thermal decomposition occurred above 240° C.

In yet another embodiment, the crystalline Form C is substantially pure.

In yet another embodiment, the crystalline Form C is chemically phase pure.

In yet another embodiment, the crystalline Form C is substantially phase pure.

In one embodiment, the invention pertains to a process for making crystalline Form C of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

a) Suspending Modification A in dichloromethane at a temperature of about 40° C. for about 3 days;
b) Letting the suspension cool down to room temperature;
c) Isolating Form C as a solid (e.g. by filtration).

In another embodiment, the invention pertains to a process for making crystalline Form C of compound N-(3-(6-Amino-5-(2-(N-methylacrylamido)ethoxy)pyrimidin-4-yl)-5-fluoro-2-methylphenyl)-4-cyclopropyl-2-fluorobenzamide, said process comprises the steps of:

a) Suspending Modification A in a solvent mixture comprising at least 50% of dichloromethane;
b) Letting the suspension equilibrate at room temperature for about 4 weeks;
c) Isolating Form C as a solid (e.g. by filtration).

In one aspect of the above embodiment, the solvent mixture is MeOH/dichloromethane 50:50 (v/v).

In another embodiment, the invention relates to a pharmaceutical composition comprising a therapeutically effective amount of a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or a combination thereof), and at least one pharmaceutically acceptable carrier, diluent or excipient. In a particular embodiment, the invention relates to a pharmaceutical composition comprising crystalline Form A, and one or more pharmaceutically acceptable carriers, diluents or excipients. In yet another aspect, the invention relates to a pharmaceutical composition comprising crystalline Form A in substantially phase pure form. In yet another aspect, the invention relates to a pharmaceutical composition comprising crystalline Form B in substantially phase pure form. In yet another embodiment, the invention relates to a pharmaceutical formulation comprising crystalline Form A and further comprising at least one other solid state form of N-(3-(6-Amino-5-(2-(N-methylacrylamido)ethoxy)pyrimidin-4-yl)-5-fluoro-2-methylphenyl)-4-cyclopropyl-2-fluorobenzamide. In one aspect of this embodiment, the other solid state form is crystalline Form B. In yet another embodiment, the other solid state form is an amorphous form of N-(3-(6-Amino-5-(2-(N-methylacrylamido)ethoxy)pyrimidin-4-yl)-5-fluoro-2-methylphenyl)-4-cyclopropyl-2-fluorobenzamide, In other embodiments, the invention relates to combinations, in particular pharmaceutical combinations, comprising a therapeutically effective amount of a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or combination thereof), and one or more therapeutic agents.

In a particular embodiment, the invention relates to a pharmaceutical combination comprising crystalline Form A, and one or more therapeutic agents. In yet another aspect, the invention relates to a pharmaceutical combination comprising crystalline Form A in substantially phase pure form and one or more therapeutic agent. In yet another aspect, the invention relates to a pharmaceutical combination comprising crystalline Form B in substantially phase pure form and one or more therapeutic agent. In yet another embodiment, the invention relates to a pharmaceutical combination comprising crystalline Form A and further comprising at least one other solid state form of N-(3-(6-Amino-5-(2-(N-methylacrylamido)ethoxy)pyrimidin-4-yl)-5-fluoro-2-methylphenyl)-4-cyclopropyl-2-fluorobenzamide. In one aspect of this embodiment, the other solid state form is crystalline Form B. In yet another embodiment, the other solid state form is an amorphous form of N-(3-(6-Amino-5-(2-(N-methylacrylamido)ethoxy)pyrimidin-4-yl)-5-fluoro-2-methylphenyl)-4-cyclopropyl-2-fluorobenzamide.

In another embodiment, the invention provides pharmaceutical combinations as described herein wherein the therapeutic agent is independently selected from the group of immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the crystalline forms of compounds of Formula (I) may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide Q-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline](WHI-P131), [4-(3'-bromo-4'-hydroxylphenyl)-amino-6,7-dimethoxyquinazoline](WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; sphingosine-1-phosphate receptor modulators such as FTY720 (fingolimod), or compounds disclosed in WO 2005/000833; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent. Further combination partners to a compound of Formula (I) may be selected from a PI3K inhibitor (e.g. pan, or alpha, beta, gamma, delta selectives), TNF inhibitors, IL1beta inhibitors, IL17 inhibitors, and inhibitors of IL6 or IL receptor.

In one embodiment, the invention relates to a method of treating a diseases or a disorder which is typically ameliorated by the inhibition of BTK, in a subject in need thereof, the method comprising: administering to a subject in need thereof, a therapeutically effective amount of a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or a combination thereof, preferably Form A), alone or in combination with one or more therapeutic agents.

In another embodiment, the invention relates to a method of treating a disease or a disorder which is typically ameliorated by the inhibition of BTK (e.g. inflammatory and autoimmune disorders and pulmonary and respiratory tract inflammation), in a subject in need thereof, comprising administering to said subject, a pharmaceutical composition as described herein, alone or in combination with one or more therapeutic agents.

In another embodiment, the invention relates to a method of treating a disease or a disorder which is typically ameliorated by the inhibition of BTK (e.g. inflammatory and autoimmune disorders and pulmonary and respiratory tract inflammation), in a subject in need thereof, comprising administering to said subject a pharmaceutical combination as described herein.

In one embodiment, the invention relates to the use of a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or a combination thereof, or preferably Form A), alone or in combination with one or more therapeutic agents, for the treatment of a disease or a disorder which is typically ameliorated by the inhibition of BTK, e.g. inflammatory and autoimmune disorders and pulmonary and respiratory tract inflammation.

In yet another embodiment, the invention pertains to a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or a combination thereof, or preferably Form A), for use in the treatment of a disease or a disorder which is typically ameliorated by the inhibition of BTK, e.g. inflammatory and autoimmune disorders and pulmonary and respiratory tract inflammation.

In yet another embodiment, the invention pertains to a combination of a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A, Form B or a combination thereof, or preferably Form A), and one or more therapeutic agents, for use in the treatment of a disease or a disorder which is typically ameliorated by the inhibition of BTK.

In one embodiment, the invention relates to a method of treatment, a use, a compound for use, or a combination for use as described herein, wherein the disease or disorder which is typically ameliorated by the inhibition of BTK is selected from inflammatory and autoimmune disorders and pulmonary and respiratory tract inflammation. More specifically, the disease or the disorder which is typically ameliorated by the inhibition of BTK is selected from autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic urticaria (chronic spontaneous urticaria, inducible urticaria), chronic allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease. Preferably, the disease or the disorder which is typically ameliorated by the inhibition of BTK is selected from rheumatoid arthritis; chronic urticaria, preferably chronic spontaneous urticaria; Sjögren's syndrome, multiple sclerosis or asthma.

Crystalline Form A described herein has been found to have advantageous properties.

Form A of compound of Formula (I) is the most stable form. Form A was physically stable when exposed to high level of % RH and upon exposure of long-term stress conditions. Form A is also stable in suspension in non-chlorinated solvent (e.g. solvent other than dichloromethane and chloroform).

Due to its non-hygroscopic behavior, the physicochemical properties if Form A of the present invention are preserved regardless of the relative humidity of the surrounding atmosphere, which facilitates easier and more reliable manufacturing processes as well as easier storage of a pharmaceutical product containing said form A. In addition, crystalline Form A preserves its crystal structure even when subjected to severe temperature and/or humidity stress conditions or when slurried for prolonged time in various solvents.

Chloroform and dichloromethane solvents were found to lead to the formation of Modification B and/or Modification C.

Modification C is a metastable form, since Modification C converts to Modification B at room temperature or by heating at 50° C.

Modification B is stable up to 170° C. but Modification B converts to Modification A above 170° C.

Pharmaceutical Composition, Dosage and Administration

In one embodiment the crystalline forms of N-(3-(6-Amino-5-(2-(N-methylacrylamido)ethoxy)pyrimidin-4-yl)-5-fluoro-2-methylphenyl)-4-cyclopropyl-2-fluorobenzamide described herein can be used alone or they can be formulated into a pharmaceutical composition that also contains at least one pharmaceutically acceptable excipient, and often contains at least two or more pharmaceutically acceptable excipients. Some suitable excipients are disclosed herein. Other excipients may be used that are known in the art without departing from the intent and scope of the present application.

In some embodiments, the present invention utilizes a pharmaceutical composition comprising a compound of the present invention and a pharmaceutically acceptable excipient.

As used herein, the term "pharmaceutically acceptable excipients" includes any and all solvents, carriers, diluents, dispersion media, coatings, surfactants, antioxidants, preservatives (e.g., antibacterial agents, antifungal agents, antioxidants), isotonic agents, absorption delaying agents, salts, drug stabilizers, binders, additives, bulking agents, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). It should be understood that unless a conventional excipient is incompatible with the active ingredient, the use of any conventional excipient in any therapeutic or pharmaceutical compositions is contemplated by the present application.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

Typically, the pharmaceutical compositions are tablets or capsules comprising the active ingredient together with at least one excipient, such as:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired;
d) carriers such as an aqueous vehicle containing a co-solvating material such as captisol, PEG, glycerin, cyclodextrin, or the like;
e) disintegrants, e.g., starches, agar, alginic acid or its sodium salt, or effervescent mixtures; and/or
f) absorbents, colorants, flavors and sweeteners.

Tablets may be either film coated or enteric coated according to methods known in the art.

Preferably, the compound or composition is prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e. g., vials), blister packs, and strip packs.

Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 10-50 mg of active ingredients. Preferably, the pharmaceutical composition or combination of the present invention can be in unit dosage of about 10 mg, about 25 mg or about 50 mg. The therapeutically effective dosage or amount of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg. Preferably, the therapeutically effective amount in vivo ranges between about 10 mg to about 200 mg daily, for example, about 10 mg, about 20 mg, about 25 mg, about 35 mg, about 50 mg, about 100 mg or about 200 mg daily. Preferably, the therapeutically effective amount in vivo is selected from about 10 mg, about 35 mg, about 50 mg or about 100 mg once a day. Also, preferably, the therapeutically effective amount in vivo is selected from about 10 mg, about 25 mg, about 50 mg or about 100 mg twice a day.

In other embodiments, a pharmaceutical composition is provided which comprises at least one crystalline form according to the embodiments herein supra (e.g. Form A, Form B or mixture thereof, preferably Form A); and at least one pharmaceutically acceptable carrier.

Accordingly, in an embodiment of the disclosure, a crystalline form of N-(3-(6-Amino-5-(2-(N-methylacrylamido)ethoxy)pyrimidin-4-yl)-5-fluoro-2-methylphenyl)-4-cyclopropyl-2-fluorobenzamide (Form A or Form B, preferably Form A) is provided in a substantially phase pure form. This crystalline form of a N-(3-(6-Amino-5-(2-(N-methylacrylamido)ethoxy)pyrimidin-4-yl)-5-fluoro-2-methylphenyl)-4-cyclopropyl-2-fluorobenzamide (Form A or Form B) in substantially phase pure form may be used to prepare pharmaceutical compositions which may further comprising one or more pharmaceutically acceptable excipients.

Combination:

The crystalline form of compound of Formula (I) of the invention (e.g. Form A or Form B or mixture thereof, preferably Form A) may be administered either simultaneously with, or before or after, one or more other therapeutic agents. The crystalline forms of the present invention may be administered separately, by the same or different route of administration, or together in the same pharmaceutical composition as the other agents.

The crystalline forms of the compound of Formula (I) may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of Formula (I) may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline](WHI-P131), [4-(3'-bromo-4'-hydroxylphenyl)-amino-6,7-dimethoxyquinazoline](WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690, 550), or a compound as disclosed in WO 04/052359 or WO 05/066156; sphingosine-1-phosphate receptor modulators such as FTY720 (fingolimod), or compounds disclosed in WO 2005/000833; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent. Further combination partners to a compound of Formula (I) may be selected from a PI3K inhibitor (e.g. pan, or alpha, beta, gamma, delta selectives), TNF inhibitors, IL1beta inhibitors, IL17 inhibitors, and inhibitors of IL6 or IL receptor.

Therapeutic Kits

In one embodiment, the invention provides a kit comprising two or more separate pharmaceutical compositions, at least one of which contains a crystalline form of the compound of Formula (I) (Form A, Form B or mixture thereof, preferably Form A). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, a crystalline form of a compound of Formula (I) (i.e. Form A, Form B or mixture thereof, preferably Form A) and the other therapeutic agent may be manufactured and/or formulated by the same or different manufacturers. Moreover, a crystalline form of the compound of Formula (I) and the other therapeutic may be brought together into a combination therapy: (i) prior to release of the combination product to physicians (e.g. in the case of a kit comprising a crystalline form of compound of Formula (I) and the other therapeutic agent); (ii) by the physician themselves (or under the guidance of the physician) shortly before administration; (iii) in the patient themselves, e.g. during sequential administration of a crystalline form of the compound of Formula (I) and the other therapeutic agent.

Accordingly, the invention provides the use of a crystalline form as described herein (i.e. i.e. Form A, Form B or mixture thereof, preferably Form A), for treating a disease ameliorated by inhibition of BTK (e.g. autoimmune diseases, anti-inflammatory diseases, respiratory disease), wherein the medicament is prepared for administration with another therapeutic agent. The invention also provides the use of a therapeutic agent for treating a disease ameliorated by inhibition of BTK (e.g. autoimmune diseases, anti-inflammatory diseases, respiratory disease), wherein the medicament is administered with a crystalline form of the compound of Formula (I).

The invention also provides a crystalline form of the compound of Formula (I) (i.e. i.e. Form A, Form B or mixture thereof, preferably Form A), for use in a method of treating disease ameliorated by BTK inhibition, wherein the crystalline form of compound of Formula (I) is prepared for administration with another therapeutic agent. The invention also provides another immunotherapeutic agent for use in a method of treating a disease ameliorated by inhibition of BTK, wherein the other therapeutic agent is prepared for administration with a crystalline form of compound of Formula (I). The invention also provides crystalline form of compound of Formula (I), for use in a method of treating a disease ameliorated by inhibition of BTK, wherein the crystalline form of compound of Formula (I) is administered with another therapeutic agent. The invention also provides another therapeutic agent for use in a method of treating a disease ameliorated by inhibition of BTK, wherein the other therapeutic agent is administered with a crystalline form of compound of Formula (I).

The invention also provides the use of a crystalline form of compound of Formula (I), for treating a disease ameliorated by inhibition of BTK (e.g. autoimmune diseases, anti-inflammatory diseases, respiratory disease), wherein the patient has previously (e.g. within 24 hours) been treated with another therapeutic agent. The invention also provides the use of another therapeutic agent for treating a disease ameliorated by inhibition of BTK (e.g. autoimmune diseases, anti-inflammatory diseases, respiratory disease), wherein the patient has previously (e.g. within 24 hours) been treated with a crystalline form of compound of Formula (I).

Preparation of Crystalline Form N-(3-(6-Amino-5-(2-(N-methylacrylamido)ethoxy)pyrimidin-4-yl)-5-fluoro-2-methylphenyl)-4-cyclopropyl-2-fluorobenzamide Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent or solvent mixture include, for example, evaporation of the solvent, decreasing the temperature of the solvent or solvent mixture, crystal seeding a supersaturated solvent mixture of the molecule and/or salt, freeze drying the solvent mixture, and addition of antisolvents (countersolvents) to the solvent mixture. Exemplary methods of preparing the crystalline forms described herein are set forth in detail below.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Indiana (1999).

For crystallization techniques that employ solvents, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature. This may also be referred to as a suspension.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Alternatively, crystalline forms may be prepared directly from the reaction medium of the final process for preparing N-(3-(6-Amino-5-(2-(N-methylacrylamido)ethoxy)pyrimidin-4-yl)-5-fluoro-2-methylphenyl)-4-cyclopropyl-2-fluorobenzamide. This may be achieved, for example, by employing in the final process step a solvent or a mixture of solvents from which N-(3-(6-Amino-5-(2-(N-methylacrylamido)ethoxy)pyrimidin-4-yl)-5-fluoro-2-methylphenyl)-4-cyclopropyl-2-fluorobenzamide may be crystallized. In addition, crystalline forms may be obtained by distillation or solvent addition techniques.

In addition to the methods discussed briefly below, it should be understood that various analytical methods may be used for the characterization of any of the materials described herein.

The following non-limiting examples are illustrative of the disclosure.

EXAMPLES

Example 1: Preparation of the Anhydrous Crystalline Form A

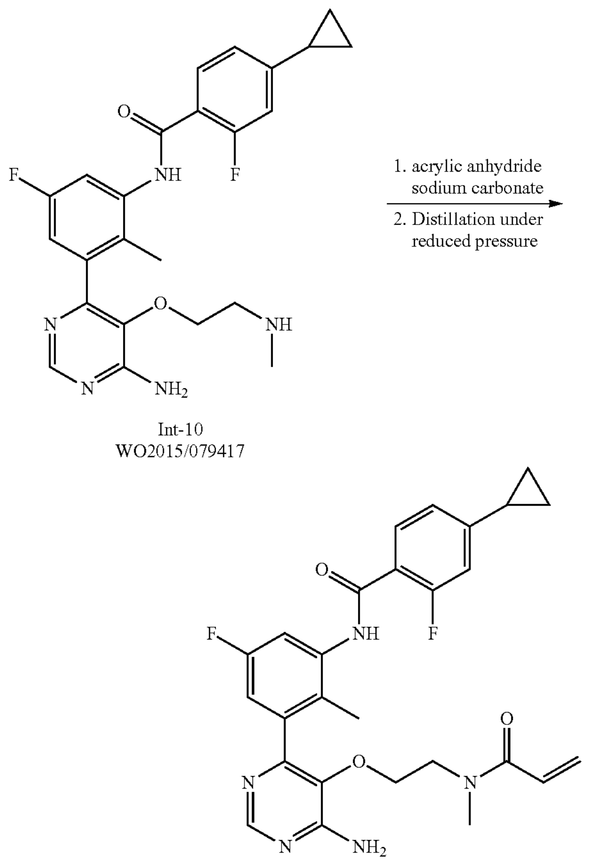

Int-10
WO2015/079417

Form A

N-(3-(6-amino-5-(2-(methylamino)ethoxy)pyrimidin-4-yl)-5-fluoro-2-methylphenyl)-4-cyclopropyl-2-fluorobenzamide (Int-10 as disclosed in WO2015/079417) and sodium carbonate were suspended in ethyl acetate and heated to 50° C. A solution of acrylic anhydride in ethyl acetate (20% w/w) was added to the suspension. The reaction mixture was stirred for about 30 min at 50° C. After addition of water, the reaction mixture was stirred for about 30 min at 65° C. Subsequently, the phases were separated at 60° C. and the aqueous phase is removed. The organic phase was washed with 0.05M sulfuric acid and the aqueous phase was removed at 60° C. Afterwards, the organic phase was washed with water and the aqueous phase was removed 60° C. The final organic phase treated by low in particles filtration. At internal temperature 60° C., a distillation was conducted at reduced pressure to remove part of the solvent mixture, while simultaneously adding ethyl acetate to keep the solvent level about constant. Thereby the water content was reduced. (Optionally, to the solution, a seed suspension of Form A in ethyl acetate is added). The suspension was stirred for at least 15 min. Afterwards further distillation with internal temperature of 60° C., was conducted at reduced pressure to remove part of the solvent mixture, while simultaneously adding ethyl acetate to keep the solvent level about constant.

The suspension was stirred for 30 min at 60° C., cooled down to 30° C. in 200 min and was stirred for 30 min at 30° C. At internal temperature of 30° C., a final distillation was conducted at reduced pressure, while simultaneously adding ethyl acetate to keep the solvent level about constant. After 120 min stirring at 30° C., the suspension was cooled down to 0° C. within 300 min and left to stir for at least 240 at 0° C. The product was isolated by centrifugation and the filter cake is washed two times with ethyl acetate. The isolated wet product was dried on trays in a drying oven at 40° C. under vacuum. Crystalline Form A was obtained. Modification A was characterized by HR-XRPD, LCMS, TGA and DSC.

Example 2: Preparation of the Anhydrous Crystalline Form C

Modification A (Example 1) was suspended in dichloromethane at 50° C. for 3 days. Afterwards, the suspension was filtered on a Buchner filter. The solid was recovered by filtration and was dired under vacuum (200 mbar) at room temperature overnight to yield Modification C. Modification C was stored at −20° C. to prevent further conversion.

Example 3: Preparation of the Anhydrous Crystalline Form B

Modification C (Example 2) was left at room temperature and the conversion into Modification B was monitored by HR-XRPD and it was complete after 5 days.

Modifications B and C were characterized by HR-XRPD, LCMS, TGA and DSC.

Example 4: High-Resolution Powder X-Ray Diffraction

The solids were finely ground in a mortar with pestle. An 8 mm boron glass capillary (0.3 mm diameter) was filled with the compound and carefully placed in the diffractometer.

The HR-XRPD patterns were collected at 296 K on a Bruker D8 Advance system equipped with LynxEye solid state detector. The radiation used for collecting the data was CuKα1 (λ=1.54056 Å) monochromatized by a germanium crystal. Diffraction data were collected in the range 4-50° 2θ for Modification A, and in the range of 3-41.5° 2θ for Modifications B and C.

TABLE 1

| X-ray powder diffraction data for anhydrous crystalline Form A | | |
|---|---|---|
| 2θ [°] | d value [Å] | Intensity [%] |
| 7.80 | 11.33 | 44 |
| 9.28 | 9.52 | 18 |
| 10.17 | 8.69 | 12 |
| 12.03 | 7.35 | 22 |
| 13.66 | 6.48 | 51 |
| 15.68 | 5.65 | 62 |
| 16.02 | 5.53 | 18 |
| 17.81 | 4.98 | 22 |
| 18.30 | 4.84 | 66 |
| 18.73 | 4.73 | 21 |
| 19.28 | 4.60 | 27 |
| 19.90 | 4.46 | 26 |
| 20.25 | 4.38 | 9 |
| 20.76 | 4.28 | 11 |
| 21.13 | 4.20 | 10 |
| 22.10 | 4.02 | 15 |
| 23.47 | 3.79 | 57 |
| 23.96 | 3.71 | 100 |
| 24.25 | 3.67 | 12 |
| 24.86 | 3.58 | 14 |
| 25.22 | 3.53 | 20 |
| 25.58 | 3.48 | 14 |
| 27.23 | 3.27 | 16 |
| 29.60 | 3.02 | 26 |

TABLE 2

| X-ray powder diffraction data for anhydrous crystalline Form B | | |
|---|---|---|
| 2θ [°] | d value [Å] | Intensity [%] |
| 5.90 | 14.96 | 29 |
| 6.78 | 13.03 | 59 |
| 7.86 | 11.24 | 35 |
| 8.35 | 10.58 | 25 |
| 11.11 | 7.96 | 62 |
| 12.10 | 7.31 | 49 |
| 12.69 | 6.97 | 37 |
| 13.07 | 6.77 | 28 |
| 13.63 | 6.49 | 19 |
| 13.93 | 6.35 | 22 |
| 14.53 | 6.09 | 19 |
| 14.86 | 5.96 | 29 |
| 15.34 | 5.77 | 16 |
| 15.83 | 5.59 | 40 |
| 16.11 | 5.50 | 19 |
| 16.42 | 5.39 | 24 |
| 16.81 | 5.27 | 21 |
| 17.05 | 5.20 | 18 |
| 17.96 | 4.94 | 57 |
| 19.05 | 4.66 | 27 |
| 19.38 | 4.58 | 21 |
| 20.22 | 4.39 | 58 |
| 20.65 | 4.30 | 39 |
| 20.99 | 4.23 | 100 |
| 21.66 | 4.10 | 24 |
| 22.32 | 3.98 | 24 |
| 22.66 | 3.92 | 30 |
| 23.38 | 3.80 | 27 |
| 24.07 | 3.69 | 75 |
| 24.92 | 3.57 | 22 |
| 25.35 | 3.51 | 43 |
| 25.71 | 3.46 | 31 |

TABLE 3

| X-ray powder diffraction data for anhydrous crystalline Form C | | |
|---|---|---|
| 2θ [°] | d value [Å] | Intensity [%] |
| 5.91 | 14.95 | 100 |
| 11.92 | 7.42 | 84 |
| 12.07 | 7.33 | 40 |
| 12.54 | 7.05 | 49 |
| 12.97 | 6.82 | 25 |
| 13.92 | 6.36 | 20 |
| 14.46 | 6.12 | 28 |
| 14.68 | 6.03 | 22 |
| 15.32 | 5.78 | 59 |
| 17.05 | 5.20 | 68 |
| 18.00 | 4.93 | 33 |
| 18.21 | 4.87 | 20 |
| 19.03 | 4.66 | 57 |
| 19.20 | 4.62 | 23 |
| 19.92 | 4.45 | 27 |
| 20.23 | 4.39 | 26 |
| 20.87 | 4.25 | 22 |
| 21.03 | 4.22 | 34 |
| 21.19 | 4.19 | 31 |
| 21.62 | 4.11 | 19 |
| 22.84 | 3.89 | 20 |
| 23.40 | 3.80 | 33 |
| 23.71 | 3.75 | 42 |
| 24.34 | 3.65 | 17 |
| 25.09 | 3.55 | 16 |
| 25.31 | 3.52 | 26 |
| 26.15 | 3.40 | 29 |
| 26.47 | 3.37 | 20 |
| 26.91 | 3.31 | 23 |
| 27.17 | 3.28 | 28 |

Example 5: Differential Scanning Calorimetry (DSC)

Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6° C.; ΔH=28.45 J/g). Samples were sealed in standard 40 µl aluminum pans, pin-holed or hermetically sealed and heated in the DSC from −20° C. to 300° C., at a heating rate of 2° C./min, 5° C./min, 10° C./min or 20° C./min. Dry $N_2$ gas, at a flow rate of 50 ml/min was used to purge the DSC equipment during the measurement.

Cycling DSC was performed with the same equipment. The sample was sealed in standard 40 µl aluminum pans, pin-holed, heated in the DSC from 20° C. to 195° C., cooled from 195° C. to −20° C. and heated again from −20° C. to 300° C. The heating and cooling rate was 10° C./min.

The accuracy of the measured sample temperature with this method is within about 1° C., and the heat of fusion can be measured within a relative error of about ±5%.

DSC measurements of Modifications A, B and C were performed between −20 and 300° C. at different heating rates in open and closed pans.

The DSC traces recorded in open pans for Modifications A, B and C are reported in FIG. 2, FIG. 5 and FIG. 8, respectively. The onset temperatures of the exo/endothermic events observed in the DSC traces are reported in Table 4, Table 5 and Table 6, respectively.

In both sets of DSC measurements, a general shift of the thermal events to higher temperatures was observed by increasing the heating rate, as well as the broadening of the events.

The DSC curves of Modification A showed the onset melting temperature in the range 193-195° in the open and closed pans, respectively. In the DSC measurements of Modification B endo/exothermic events between 170-180° C. could be associated to the melting of Modification B and recrystallization to A.

In the DSC trace of Modification C, the presence of endo/thermic events between 170 and 180° C. confirmed that by heating Modification C converted to Modification B

TABLE 4 onset temperature and enthalpy value for the endothermic event determined in the DSC measurements performed on Modification A in open pan at 2, 5, 10 and 20° C./min heating rate.

| Heating rate (° C./min) | Onset Endo (° C.) | ΔH (J/g) |
|---|---|---|
| 2 | 193.2 | 95 |
| 5 | 194.0 | 120 |
| 10 | 194.2 | 118 |
| 20 | 195.4 | 106 |

TABLE 5 onset temperature and enthalpy value for the endo- and exothermic events determined in the DSC measurements performed on Modification B in open pan at 2, 5, 10 and 20° C./min heating rate.

| Heating rate (° C./min) | Onset $Endo_1$ (° C.) | ΔH (J/g) | Onset $Exo_2$ (° C.) | ΔH (J/g) | Onset $Endo_3$ (° C.) | ΔH (J/g) |
|---|---|---|---|---|---|---|
| 2 | 169.6 | 13 | 172.3 | 12 | 194.0 | 112 |
| 5 | 169.9 | 17 | 173.5 | 15 | 194.5 | 119 |
| 10 | 170.5 | 24 | 175.1 | 22 | 194.8 | 112 |
| 20 | 171.0 | 26 | 178.8 | 22 | 195.3 | 112 |

TABLE 6 onset temperature and enthalpy value for the endo- and exothermic events determined in the DSC measurements performed on Modification C in open pan at 2, 5, 10 and 20° C./min heating rate

| Heating rate (° C./min) | Onset $Exo_1$ (° C.) | ΔH (J/g) | Onset $Endo_1$ (° C.) | ΔH (J/g) | Onset $Endo_2$ (° C.) | ΔH (J/g) | Onset $Endo_3$ (° C.) | ΔH (J/g) |
|---|---|---|---|---|---|---|---|---|
| 2 | — | — | 170.4 | 28 | 172.3 | 23 | 193.5 | 112 |
| 5 | — | — | 170.9 | 28 | 173.6 | 27 | 194.6 | 110 |
| 10 | — | — | 171.3 | 31 | 175.5 | 26 | 195.5 | 102 |
| 20 | 98.6 | 4 | 171.8 | 43 | 177.5 | 31 | 195.4 | 99 |

Example 6: Thermogravimetric Analysis (TGA)

Mass loss due to solvent or water loss from the crystals was determined by TGA/SDTA (single differential thermal analysis) and TGMS (thermogravimetric analysis coupled with Mass Spectroscopy). Monitoring the sample weight, during heating in a TGA/DSC 3+ STARe system (Mettler-Toledo GmbH, Switzerland), resulted in a weight vs. temperature curve. The TGA/DSC 3+ was calibrated for temperature with samples of indium and aluminum. Samples (circa 2 mg) were weighed into 100 μL aluminum crucibles and sealed. The seals were pin-holed, and the crucibles heated in the TGA from 25 to 300° C. at a heating rate of 10° C./min. Dry $N_2$ gas was used for purging. The gases coming from the TGA samples were analyzed by a mass spectrometer Omnistar GSD 301 T2 (Pfeiffer Vacuum GmbH, Germany). The latter is a quadrupole mass spectrometer, which analyzes masses in the temperature range of 0-200 amu. Temperatures are reported in degrees Celsius (° C.) and weight loss in %.

The TGA/SDTA analysis of the Modification A (FIG. 3) revealed a mass loss of 0.3% in the range 40-200° C., indicating that Modification A was anhydrous. The endothermic peak around 190° C. in the SDTA curve could be attributed to the melting of the compound. Thermal degradation occurred above 240° C.

FIG. 3. TGA/SDTA analysis (heating rate of 10° C./min) of Modification A. A mass loss of 0.3% was recorded in the range 40-200° C. Thermal decomposition occurred above 240° C.

The TGA/STDA analysis of Modification B (FIG. 6) revealed a mass loss of 0.2% in the range 40-160° C. Therefore, Modification B was anhydrous. The events occurring above 160° C. in the SDTA curve is attributed to melting of Modification B and recrystallization into Modification A, followed by the final melting of Modification A. Thermal degradation occurred above 240° C.

Figure 6:
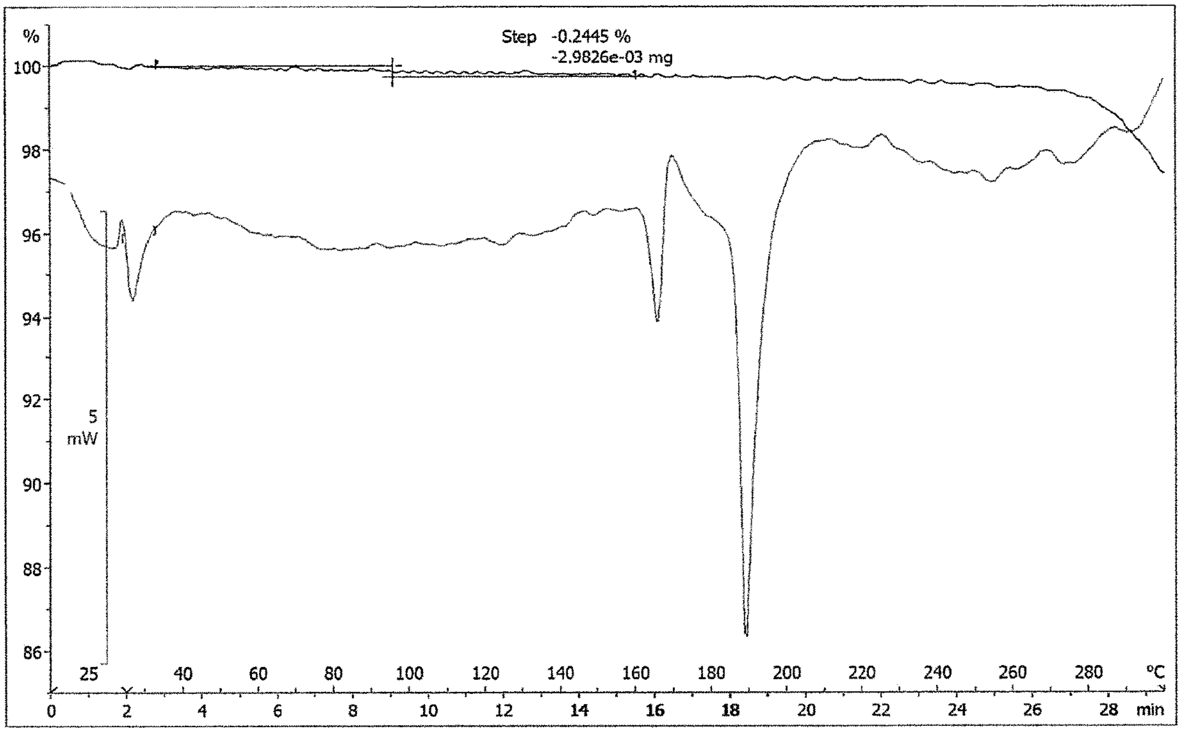
FIG. 6 provides an illustrative TGA for an anhydrous crystalline form of the compound of Formula (I), designated herein as Form B.

FIG. 6. TGA/SDTA (analysis (heating rate of 10° C./min) of the Modification B. A mass loss of 0.2% was recorded in the range 40-160° C. Thermal decomposition occurred above 240° C.

The TGMS analysis of Modification C (FIG. 9) revealed a mass loss of 0.01% in the range 40-150° C., indicating that Modification C was an anhydrous crystalline phase. Thermal degradation occurred above 240° C.

Figure 9:
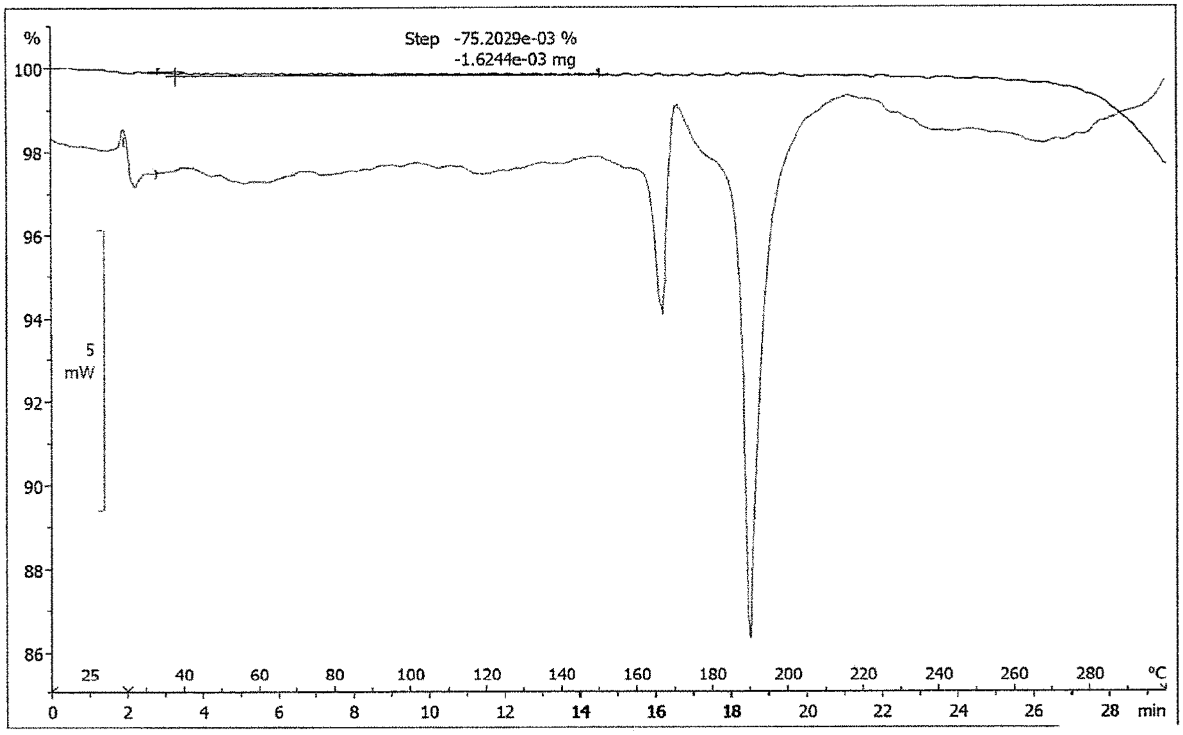
FIG. 9 provides an illustrative TGA for an anhydrous crystalline form of the compound of Formula (I), designated herein as Form C.

FIG. 9. TGA/SDTA (20A) and TGMS (20B) analysis (heating rate of 10° C./min) of the Modification C. A mass loss of 0.01% was recorded in the range 40-150° C. Thermal decomposition occurred above 240° C.

Example 4: Physico-Chemical Stability Comparison

Modifications A, B and C were subjected to the following stress conditions:

80° C. in closed vials for 1 month;

80° C./75% RH in open vials for 1 month;

100° C. in closed vials for 3 days;

Afterwards, the solids were analyzed by HR-XRPD, TGMS and HPLC assay to evaluate potential solid phase change, loss on drying and chemical purity.

Upon completion of the stability test, all solids were analyzed by HR-XRPD, TGMS and HPLC assay. The results of the physico-chemical stability test are reported in Table 7.

HPLC Conditions

Auto sampler temp.: 15° C.

Column: Waters Sunfire C18 (100×4.6 mm; 3.5 μm).

Column temp: 35° C.

Flow cell: 10 mm path

Gradient: Mobile phase A: 0.1% TFA in Water

Mobile phase B: 0.1% TFA in Acetonitrile

Flow: 1.0 ml/min

| Gradient: | | |
|---|---|---|
| Time [min]: | Eluent A: | Eluent B: |
| 0 | 90% | 10% |
| 9 | 10% | 90% |
| 10 | 90% | 10% |
| 11 | 90% | 10% |

Run time: 11 min

TABLE 7

Results of the physico-chemical stability tests performed on Modifications A, B and C.

| Starting Modification | Stress conditions | HR-XRPD recovered solid | Loss on drying (%) | HPLC assay recovery (%) |
|---|---|---|---|---|
| A | 80° C., 1 month, closed vial | A | 0.003 | 98.0 |
| B | 80° C., 1 month, closed vial | B | 0.009 | 99.8 |
| C | 80° C., 1 month, closed vial | B | 0.007 | 101.8 |
| A | 80° C./75% RH, 1 month, open vial | A | 0.003 | 104.5 |
| B | 80° C./75% RH, 1 month, open vial | B | 0.004 | 102.5 |
| C | 80° C./75% RH, 1 month, open vial | B | 0.006 | 100.3 |
| A | 100° C., 3 days, closed vial | A | 0.003 | 98.4 |
| B | 100° C., 3 days, closed vial | B | 0.004 | 103.0 |
| C | 100° C., 3 days, closed vial | B | 0.003 | 99.7 |

After exposure to 80° C. for 1 month and 100° C. for 3 days, Modification C converted to Modification B. The XRPD patterns of Modifications A and B were unchanged. On the contrary, Modification C converted to Modification B under all the three test conditions.

The TGMS analysis did not show any significant moisture uptake, therefore the solids were not hygroscopic.

The chemical purity of the samples was not affected by exposure to high temperatures and high RH levels for 3 days or for 1 month, as indicated by the recovery values which were close to 100%.

Example 5: Hydroscopicity Studies

Moisture Uptake of Modification A

The moisture sorption of Modification A was evaluated by exposing the solid material to 80% and 92% RH at 25° C. for 24 hours. Afterwards, the solids were analyzed by HT-XRPD to evaluate any change in crystalline phase, and by TGMS to determine the water uptake. Modification A was physically stable after exposure to 80 and 92% RH for 24 hours. The TGMS analysis revealed a mass loss of 0.2% for both samples. Therefore, Modification A could be considered non-hygroscopic.

Moisture Sorption Isotherms of Modification A at 250 and 40° C.

Dynamic vapor sorption (DVS): Moisture sorption isotherms were collected on a DVS-1 system from Surface Measurement Systems (London, UK). Typical sample size was between 5 and 10 mg of solid material. The relative humidity profile was 40→0→95→0→95→40% with an increase of 10% RH level per step. Weight equilibration time was set for a minimum holding time of 60 minutes and a maximum of 6 hours per relative humidity step, and with a dm/dt 0.002%/min.

Dynamic vapor sorption (DVS) measurements were carried out on Modification A at 25° and 40° C., with the RH profile 40→0→95→0→95→40% in steps of 10% RH.

Modification A did not show significant water vapor uptake both at 25° and 40° C. At 95% RH the highest change in mass was 0.4% and 0.3% at 25 and 40° C., respectively. The sorption and desorption cycles were reversible, and no indication of hydrate formation was gained by the DVS measurements. The solid recovered after DVS measurements were still Modification A.

DVS Measurements of Modifications B and C

The DVS measurements carried out on Modifications B and C provided similar results as collected for Modification A. Both crystalline phases did not show significant water vapor uptake.

The highest mass gain recorded at 95% RH was 0.3% for both phases.

The XRPD pattern of Modification B was unchanged after DVS measurement. On the contrary, the solid recovered after DVS measurement of Modification C was a mixture of Modifications B and C, probably due to the spontaneous conversion of Modification C to B at 25° C.

Example 5: Stability in Solvent

Stability of Modification A in Solvent

Suspensions of Modification A were prepared in 23 selected solvents and let to equilibrate at room temperature (RT) for 4 weeks and at 50° C. for 2 weeks. Upon completion of the equilibration time, the solids were separated from the liquid phases, dried at ambient conditions and under vacuum (5 mbar/50° C.), and analyzed by HT-XRPD.

When the suspensions dissolved, the solvent was removed by evaporation under vacuum (initially at 200 mbar/RT, then at 5 mbar/50° C.). The liquid phases were also evaporated under the same conditions. Residual solids were analyzed by HT-XRPD.

The experimental details and results of the solvent equilibration experiments performed at RT and 50° C. can be found in Table 8 and Table 9, respectively.

TABLE 8

Experimental conditions and results for the solvent equilibration experiments performed on Modification A at RT for 4 weeks.

| | | | | | HT-XRPD | | |
|---|---|---|---|---|---|---|---|
| Mass (mg) | Solvent | Volume (uL) | Concentration (mg/mL) | Solid after profile | Ambient Dried | Vacuum dried | Evap. ML |
| 101.3 | 1,4-Dioxane | 500 | 202.6 | Yes | A | A | — |
| 103.2 | 2-Methyl-2-butanol | 500 | 206.4 | Yes | A | A | — |
| 96.1 | Acetone | 500 | 192.2 | Yes | A | A | — |
| 91.9 | Acetonitrile | 500 | 183.8 | Yes | A | A | — |
| 102.9 | Anisole | 500 | 205.8 | Yes | A | A | — |
| 100.8 | Chloroform | 500 | 201.6 | Yes | C | B | B |
| 102.0 | Cyclopentanone | 500 | 204.0 | Yes | A | A | — |
| 104.0 | DCM | 500 | 208.0 | Yes | C | B + C | — |
| 103.2 | DMSO | 500 | 206.4 | No | — | — | A |
| 105.7 | Ethanol | 500 | 211.4 | Yes | A | A | — |
| 107.4 | Isopropyl acetate | 500 | 214.8 | Yes | A | A | — |
| 102.2 | MeOH | 500 | 204.4 | Yes | A | A | A (l.y.) |
| 102.9 | MeOH/Acetone 50/50 | 500 | 205.8 | Yes | A | A | A (l.y.) |
| 91.3 | MeOH/Chloroform 50/50 | 500 | 182.6 | Yes | A | A | A |
| 93.8 | MeOH/DCM 50/50 | 500 | 187.6 | Yes | C | B + C | B (l.y.) |
| 108.3 | MeOH/1,4-Dioxane 50/50 | 500 | 216.6 | Yes | A | A | A |
| 101.3 | MeOH/Pyridine 50/50 | 500 | 202.6 | Yes | A | A | A |
| 99.6 | MeOH/THF 50/50 | 500 | 199.2 | Yes | A | A | A |
| 105.2 | Nitromethane | 500 | 210.4 | Yes | A | A | — |
| 174.0 | 1-Methyl-2-pyrrolidinone | 500 | 348.0 | Yes | A | A | A |
| 93.4 | Pyridine | 500 | 186.8 | Yes | A | A | A |
| 91.3 | THF | 500 | 182.6 | Yes | A | A | A |
| 101.0 | Water | 500 | 202.0 | Yes | A | A | — |

The notation (—) indicates that no solid was recovered.
The notation (l.y.) indicates that poor amount (low yield) of material was recovered.
ML is mother liquor.

TABLE 9

Experimental conditions and results for the solvent equilibration experiments performed on Modification A at 50° C. for 2 weeks.

| | | | | | HT-XRPD | | |
|---|---|---|---|---|---|---|---|
| Mass (mg) | Solvent | Volume (uL) | Concentration (mg/mL) | Solid after profile | Ambient Dried | Vacuum dried | Evap. ML |
| 103.9 | 1,4-Dioxane | 500 | 207.8 | Yes | A | A | A |
| 91.7 | 2-Methyl-2-butanol | 500 | 183.4 | Yes | A | A | — |
| 94.0 | Acetone | 500 | 188.0 | Yes | A | A | A (l.y.) |
| 100.4 | Acetonitrile | 500 | 200.8 | Yes | A | A | A (l.y.) |
| 93.2 | Anisole | 500 | 186.4 | Yes | A | A | A (l.y.) |
| 93.8 | Chloroform | 500 | 187.6 | Yes | A | A | A + B |
| 97.6 | Cyclopentanone | 500 | 195.2 | Yes | A | A | A |
| 99.6 | DCM | 500 | 199.2 | Yes | C | B | B |
| 90.4 | DMSO | 500 | 180.8 | No | — | — | A |
| 92.5 | Ethanol | 500 | 185.0 | Yes | A | A | A |
| 97.9 | Isopropyl acetate | 500 | 195.8 | Yes | A | A | A (l.y.) |
| 98.1 | MeOH | 500 | 196.2 | Yes | A | A | A |
| 95.2 | MeOH/Acetone 50/50 | 500 | 190.4 | Yes | A | A | A |
| 100.9 | MeOH/Chloroform 50/50 | 500 | 201.8 | No | — | — | A |
| 98.9 | MeOH/DCM 50/50 | 500 | 197.8 | No | — | — | B |

TABLE 9-continued

Experimental conditions and results for the solvent equilibration experiments performed on Modification A at 50° C. for 2 weeks.

| Mass (mg) | Solvent | Volume (uL) | Concentration (mg/mL) | Solid after profile | HT-XRPD Ambient Dried | Vacuum dried | Evap. ML |
|---|---|---|---|---|---|---|---|
| 94.8 | MeOH/1,4-Dioxane 50/50 | 500 | 189.6 | Yes | A | A | A |
| 98.5 | MeOH/Pyridine 50/50 | 500 | 197.0 | Yes | A | A | A |
| 95.2 | MeOH/THF 50/50 | 500 | 190.4 | Yes | A | A | A |
| 99.1 | Nitromethane | 500 | 198.2 | Yes | A | A | A (l.y.) |
| 191.3 | 1-Methyl-2-pyrrolidinone | 500 | 382.6 | No | — | — | A |
| 97.0 | Pyridine | 500 | 194.0 | Yes | A | A | A |
| 101.4 | THF | 500 | 202.8 | Yes | A | A | A |
| 97.3 | Water | 500 | 194.6 | Yes | A | A | A (l.y.) |

The notation (—) indicates that no solid was recovered.
The notation (l.y.) indicates that poor amount of material was recovered.

Stability of Modifications B and C in Solvent

Suspensions of Modifications B and C were prepared in 15 selected solvents and let to equilibrate at RT for 2 weeks and at 50° C. for 1 week. Upon completion of the equilibration time, the solids were separated from the liquid phases, dried at ambient conditions and under vacuum (5 mbar/50° C.), and analyzed by HT-XRPD.

When the suspensions dissolved, the solvent was removed by evaporation under vacuum (initially 200 mbar/RT, then 5 mbar/50° C.). The liquid phases were also evaporated under the same conditions. Residual solids were analyzed by HT-XRPD.

The experimental details and results of the solvent equilibration experiments performed at RT and 50° C. on Modification B are reported in Table 10 and Table 11, respectively.

The experimental details and results of the solvent equilibration experiments performed at RT and 50° C. on Modification C are reported in Table 12 and Table 13, respectively.

TABLE 10

Experimental conditions and results for the solvent equilibration experiments performed on Modification B at RT for 2 weeks.

| Mass (mg) | Solvent | Volume (uL) | Concentration (mg/mL) | Solid after profile | HT-XRPD Ambient Dried | Vacuum dried | Evap. ML |
|---|---|---|---|---|---|---|---|
| 61.8 | 1,4-Dioxane | 600 | 103.0 | Yes | A | A | A |
| 61.4 | 2-Methyl-2-butanol | 800 | 76.8 | Yes | A | A | A |
| 61.5 | Acetone | 600 | 102.5 | Yes | A | A | — |
| 57.4 | Acetonitrile | 700 | 82.0 | Yes | A | A | — |
| 58.8 | Anisole | 600 | 98.0 | Yes | A | A | A (l.y.) |
| 59.3 | Chloroform | 700 | 84.7 | Yes | A (l.y) | (l.c.) | B |
| 57.6 | Cyclopentanone | 600 | 96.0 | Yes | A | A | — |
| 62.3 | Dichloromethane | 1000 | 62.3 | Yes | C (l.c.) | B + C | B + $S_B$ (l.y.) |
| 64.2 | Ethanol | 600 | 107.0 | Yes | A | A | — |
| 61.5 | Isopropyl acetate | 600 | 102.5 | Yes | A | A | — |
| 62.1 | Methanol | 600 | 103.5 | Yes | A | A | A |
| 59.6 | Nitromethane | 700 | 85.1 | Yes | A | A | A (l.y.) |
| 62.1 | Pyridine | 300 | 207.0 | Yes | A | A | A |
| 61.2 | Tetrahydrofuran | 600 | 102.0 | Yes | A | A | A |
| 60.0 | Water | 1000 | 60.0 | Yes | A | A | — |

The notation (—) indicates that no solid was recovered.
The notation (l.y.) indicates that poor amount of material was recovered.
The notation (l.c.) indicates that poor crystalline material was recovered.
($S_B$: solvated form)

TABLE 11

Experimental conditions and results for the solvent equilibration experiments performed on Modification B at 50° C. for 1 week.

| Mass (mg) | Solvent | Volume (uL) | Concentration (mg/mL) | Solid after profile | HT-XRPD Ambient Dried | Vacuum dried | Evap. ML |
|---|---|---|---|---|---|---|---|
| 64.7 | 1,4-Dioxane | 400 | 161.8 | Yes | A | A | A |
| 62.9 | 2-Methyl-2-butanol | 600 | 104.8 | Yes | A | A | — |
| 60.7 | Acetone | 400 | 151.8 | Yes | A | A | A |
| 58.5 | Acetonitrile | 500 | 117.0 | Yes | A | A | A (l.y.) |
| 59.3 | Anisole | 400 | 148.3 | Yes | A | A | — |
| 60.5 | Chloroform | 400 | 151.3 | Yes | A | A | A |
| 63.8 | Cyclopentanone | 400 | 159.5 | Yes | A | A | A |
| 58.1 | Dichloromethane | 800 | 72.6 | Yes | C | B + C | B + C |
| 59.3 | Ethanol | 400 | 148.3 | Yes | A | A | A (l.y.) |
| 60.6 | Isopropyl acetate | 400 | 151.5 | Yes | A | A | A (l.y.) |
| 58.8 | Methanol | 400 | 147.0 | Yes | A | A | A |
| 64.4 | Nitromethane | 500 | 128.8 | Yes | A | A | A |
| 58.1 | Pyridine | 200 | 290.5 | Yes | A | A | A |
| 60.1 | Tetrahydrofuran | 400 | 150.3 | Yes | A | A | A |
| 59.3 | Water | 1000 | 59.3 | Yes | A | A | — |

The notation (—) indicates that no solid was recovered.
The notation (l.y.) indicates that poor amount of material was recovered.

TABLE 12

Experimental conditions and results for the solvent equilibration experiments performed on Modification C at RT for 2 weeks.

| Mass (mg) | Solvent | Volume (uL) | Concentration (mg/mL) | Solid after profile | HT-XRPD Ambient Dried | Vacuum dried | Evap. ML |
|---|---|---|---|---|---|---|---|
| 70.1 | 1,4-Dioxane | 700 | 100.1 | Yes | A | A | A |
| 66.6 | 2-Methyl-2-butanol | 700 | 95.1 | Yes | A | A | — |
| 65.3 | Acetone | 700 | 93.3 | Yes | A | A | — |
| 63.9 | Acetonitrile | 700 | 91.3 | Yes | A | A | — |
| 65.1 | Anisole | 700 | 93.0 | Yes | A | A | A (l.y.) |
| 66.4 | Chloroform | 700 | 94.9 | Yes | C + $S_C$ | B | C + $S_C$ |
| 63.9 | Cyclopentanone | 500 | 127.8 | Yes | A | A | A (l.y) |
| 65.0 | Dichloromethane | 500 | 130.0 | Yes | C | B + C | — |
| 64.3 | Ethanol | 700 | 91.9 | Yes | A | A | A (l.y.) |
| 66.3 | Isopropyl acetate | 700 | 94.7 | Yes | A | A | A (l.y.) |
| 69.6 | Methanol | 500 | 139.2 | Yes | A | A | A (l.y.) |
| 65.6 | Nitromethane | 700 | 93.7 | Yes | A | A | A (l.y.) |
| 67.2 | Pyridine | 300 | 224 | Yes | A | A | A |
| 65.6 | Tetrahydrofuran | 500 | 131.2 | Yes | A | A | A |
| 65.2 | Water | 1000 | 65.2 | Yes | A | A | A (l.y.) |

The notation (—) indicates that no solid was recovered.
The notation (l.y.) indicates that poor amount of material was recovered.
($S_C$: solvated form)

TABLE 13

Experimental conditions and results for the solvent equilibration experiments performed on Modification C at 50° C. for 1 week.

| Mass (mg) | Solvent | Volume (uL) | Concentration (mg/mL) | Solid after profile | HT-XRPD Ambient Dried | Vacuum dried | Evap. ML |
|---|---|---|---|---|---|---|---|
| 67.6 | 1,4-Dioxane | 500 | 135.2 | Yes | A | A | A |
| 64.8 | 2-Methyl-2-butanol | 500 | 129.6 | Yes | A | A | A (l.y.) |
| 65.3 | Acetone | 500 | 130.6 | Yes | A | A | A (l.y.) |
| 68.7 | Acetonitrile | 500 | 137.4 | Yes | A | A | A (l.y.) |
| 68.0 | Anisole | 500 | 136.0 | Yes | A | A | — |

TABLE 13-continued

Experimental conditions and results for the solvent equilibration experiments performed on Modification C at 50° C. for 1 week.

| | | | | | HT-XRPD | | |
|---|---|---|---|---|---|---|---|
| Mass (mg) | Solvent | Volume (uL) | Concentration (mg/mL) | Solid after profile | Ambient Dried | Vacuum dried | Evap. ML |
| 64.1 | Chloroform | 500 | 128.2 | No | — | — | $S_C$ |
| 66.0 | Cyclopentanone | 300 | 220.0 | Yes | A | A | A |
| 65.8 | Dichloromethane | 300 | 219.3 | Yes | C | B | C (l.y.) |
| 68.5 | Ethanol | 500 | 137.0 | Yes | A | A | A (l.y.) |
| 65.3 | Isopropyl acetate | 500 | 130.6 | Yes | A | A | — |
| 64.3 | Methanol | 300 | 214.3 | Yes | A | A | A |
| 65.2 | Nitromethane | 500 | 130.4 | Yes | A | A | A (l.y.) |
| 67.2 | Pyridine | 150 | 448.0 | Yes | A | A | A |
| 66.7 | Tetrahydrofuran | 300 | 222.3 | Yes | A | A | A |
| 66.8 | Water | 1000 | 66.8 | Yes | A | A | — |

The notation (l.y.) indicates that poor amount of material was recovered.
The notation (—) indicates that no solid was recovered.

Example 6: Stability Under Granulation Simulation Experiments

Granulating solvents were added drop wise to polymorphic Form A until solid is wetted sufficiently. The suspension was stirred by Vortex between each addition. The suspension was dried under vacuum. The remaining solid form was isolated and degree of crystallinity was analyzed by XRPD and/or DSC. The tested Granulating solvents were water, ethanol, 2-propanol, Acetone, benzylalcohol. No change of crystallinity was observed.

Example 7: Stability Under Compression 100-300 mg of polymorphic Form A was compressed for 5 minutes at 10 tons with a hydraulic press (diameter of the tablets 13 mm). The sample was then analyzed by XRPD and DSC to check for any occurring polymorphic change. The analysis revealed no change to the material.

It was discovered that modification A of compound of Formula (I) is the most stable form. Modification A was physically stable when exposed to high level of % RH and upon exposure of long-term stress conditions. Modification A was stable under compression and granulation simulation experiments. Modification A is stable in most solvents except for chlorinated solvent such as chloroform and dichloromethane or except for mixture of solvents containing more than 50% by volume of chlorinated solvent (e.g. dichloromethane and/or chloroform). Chlorinated solvents such as Chloroform and dichloromethane solvents were found to lead to the formation of Modifications B and C. Both Modifications B and C are metastable forms, since Modification C converts to Modification B at room temperature or by heating at 50° C. and Modification B converts to Modification A above 170° C.

The invention claimed is:

1. A crystalline form of N-(3-(6-amino-5-(2-(N-methylacrylamido) ethoxy) pyrimidin-4-yl)-5-fluoro-2-methylphenyl)-4-cyclopropyl-2-fluorobenzamide, having an x-ray powder diffraction pattern comprising peaks at 9.28±0.2 °2θ, 10.17±0.2 °2θ, and 18.73±0.2 °2θ, using CuKα1 (λ=1.54056 Å) radiation at about 296 K.

2. The crystalline form of claim 1, wherein the x-ray powder diffraction pattern further comprises at least one peak selected from the group consisting of peaks at 7.80±0.2 °2θ, 12.03±0.2 °2θ, 13.66±0.2 °2θ, 15.68±0.2 °2θ, 16.02±0.2 °2θ, 17.81±0.2 °2θ, 18.30±0.2 °2θ, 19.28±0.2 °2θ, 19.90±0.2 °2θ, 20.25±0.2 °2θ, 20.76±0.2 °2θ, 21.13±0.2 °2θ, 22.10±0.2 °2θ, 23.47±0.2 °2θ, 23.96±0.2 °2θ, 24.25±0.2 °2θ, 24.86±0.2 °2θ, 25.22±0.2 °2θ, 25.58±0.2 °2θ, 27.23±0.2 °2θ, and 29.60±0.2 °2θ, using CuKα1 (λ=1.54056 Å) radiation at about 296 K.

3. The crystalline form of claim 1, wherein the x-ray powder diffraction pattern further comprises at least two peaks selected from the group consisting of peaks at 7.80±0.2 °2θ, 12.03±0.2 °2θ, 13.66±0.2 °2θ, 15.68±0.2 °2θ, 16.02±0.2 °2θ, 17.81±0.2 °2θ, 18.30±0.2 °2θ, 19.28±0.2 °2θ, 19.90±0.2 °2θ, 20.25±0.2 °2θ, 20.76±0.2 °2θ, 21.13±0.2 °2θ, 22.10±0.2 °2θ, 23.47±0.2 °2θ, 23.96±0.2 °2θ, 24.25±0.2 °2θ, 24.86±0.2 °2θ, 25.22±0.2 °2θ, 25.58±0.2 °2θ, 27.23±0.2 °2θ, and 29.60±0.2 °2θ, using CuKα1 (λ=1.54056 Å) radiation at about 296 K.

4. The crystalline form of claim 1, wherein the x-ray powder diffraction pattern further comprises at least three peaks selected from the group consisting of peaks at 7.80±0.2 °2θ, 12.03±0.2 °2θ, 13.66±0.2 °2θ, 15.68±0.2 °2θ, 16.02±0.2 °2θ, 17.81±0.2 °2θ, 18.30±0.2 °2θ, 19.28±0.2 °2θ, 19.90±0.2 °2θ, 20.25±0.2 °2θ, 20.76±0.2 °2θ, 21.13±0.2 °2θ, 22.10±0.2 °2θ, 23.47±0.2 °2θ, 23.96±0.2 °2θ, 24.25±0.2 °2θ, 24.86±0.2 °2θ, 25.22±0.2 °2θ, 25.58±0.2 °2θ, 27.23±0.2 °2θ, and 29.60±0.2 °2θ, using CuKα1 (λ=1.54056 Å) radiation at about 296 K.

5. The crystalline form of claim 1, wherein the x-ray powder diffraction pattern further comprises at least five peaks selected from the group consisting of peaks at 7.80±0.2 °2θ, 12.03±0.2 °2θ, 13.66±0.2 °2θ, 15.68±0.2 °2θ, 16.02±0.2 °2θ, 17.81±0.2 °2θ, 18.30±0.2 °2θ, 19.28±0.2 °2θ, 19.90±0.2 °2θ, 20.25±0.2 °2θ, 20.76±0.2 °2θ, 21.13±0.2 °2θ, 22.10±0.2 °2θ, 23.47±0.2 °2θ, 23.96±0.2 °2θ, 24.25±0.2 °2θ, 24.86±0.2 °2θ, 25.22±0.2 °2θ, 25.58±0.2 °2θ, 27.23±0.2 °2θ, and 29.60±0.2 °2θ, using CuKα1 (λ=1.54056 Å) radiation at about 296 K.

6. The crystalline form of claim 1, wherein the x-ray powder diffraction pattern further comprises peaks at 15.68±0.2 °2θ, 18.30±0.2 °2θ, and 23.96±0.2 °2θ, using CuKα1 (λ=1.54056 Å) radiation at about 296 K.

7. The crystalline form of claim 1 wherein the x-ray powder diffraction pattern further comprisesing peaks at 13.66±0.2 °2θ, 15.68±0.2 °2θ and 18.30±0.2 °2θ, using CuKα1 (λ=1.54056 Å) radiation at about 296 K.

8. The crystalline form of claim 1 wherein the x-ray powder diffraction spectrum is substantially the same as that shown in FIG. 1, using CuKα1 (λ=1.54056 Å) radiation at about 296 K.

9. The crystalline form of claim 1, having a differential thermogravimetric profile measured by Differential Scanning calorimetry (DSC) with a heating rate of 10° C./min, with a single endothermic peak starting at about 194° C.

10. A crystalline form of N-(3-(6-amino-5-(2-(N-methylacrylamido) ethoxy) pyrimidin-4-yl)-5-fluoro-2-methylphenyl)-4-cyclopropyl-2-fluorobenzamide, having a differential thermogravimetric profile measured by Differential Scanning calorimetry (DSC) with a heating rate of 10° C./min, with a single endothermic peak starting at about 194° C.

11. The crystalline form of claim 10, having a DSC thermogram substantially the same as that shown in FIG. 2.

12. The crystalline form of claim 1, having a DSC thermogram substantially the same as that shown in FIG. 2.

13. The crystalline form of claim 1, having a decomposition point greater than 240° C. and a weight loss on drying of about 0.3% in a temperature range of 40-200° C., as determined by thermogravimetric analysis (TGA).

14. A crystalline form of N-(3-(6-Amino-5-(2-(N-methylacrylamido) ethoxy) pyrimidin-4-yl)-5-fluoro-2-methylphenyl)-4-cyclopropyl-2-fluorobenzamide, having a decomposition point greater than 240° C. and a weight loss on drying of about 0.3% in a temperature range of 40-200° C., as determined by thermogravimetric analysis (TGA).

15. The crystalline form of claim 13, having a TGA diagram substantially the same as that shown in FIG. 3.

16. A pharmaceutical composition comprising the crystalline form of claim 1 and a pharmaceutically acceptable carrier.

17. A pharmaceutical composition comprising a therapeutically effective amount of the crystalline form of claim 1 and a pharmaceutically acceptable carrier.

18. The pharmaceutical composition of claim 17, which is a tablet.

19. A pharmaceutical composition comprising the crystalline form of claim 3 and a pharmaceutically acceptable carrier.

20. A pharmaceutical composition comprising a therapeutically effective amount of the crystalline form of claim 3 and a pharmaceutically acceptable carrier.

21. The pharmaceutical composition of claim 20, which is a tablet.

22. A pharmaceutical composition comprising the crystalline form of claim 6 and a pharmaceutically acceptable carrier.

23. A pharmaceutical composition comprising a therapeutically effective amount of the crystalline form of claim 6 and a pharmaceutically acceptable carrier.

24. The pharmaceutical composition of claim 23, which is a tablet.

25. A method of treating chronic urticaria, comprising administering to a subject in need thereof a therapeutically effective amount of the crystalline form of claim 1.

26. A method of treating chronic urticaria, comprising administering to a subject in need thereof a therapeutically effective amount of the crystalline form of claim 3.

27. A method of treating chronic urticaria, comprising administering to a subject in need thereof a therapeutically effective amount of the crystalline form of claim 6.

28. A method of treating chronic urticaria, comprising administering to a subject in need thereof the pharmaceutical composition of claim 18.

29. A method of treating chronic urticaria, comprising administering to a subject in need thereof the pharmaceutical composition of claim 21.

30. A method of treating chronic urticaria, comprising administering to a subject in need thereof the pharmaceutical composition of claim 24.

31. The method of claim 25, wherein the chronic urticaria is chronic spontaneous urticaria.

32. The method of claim 26, wherein the chronic urticaria is chronic spontaneous urticaria.

33. The method of claim 27, wherein the chronic urticaria is chronic spontaneous urticaria.

34. A method of treating chronic spontaneous urticaria, comprising administering to a subject in need thereof the pharmaceutical composition of claim 18.

35. A method of treating chronic spontaneous urticaria, comprising administering to a subject in need thereof the pharmaceutical composition of claim 21.

36. A method of treating chronic spontaneous urticaria, comprising administering to a subject in need thereof the pharmaceutical composition of claim 24.

37. The method of claim 25, wherein the chronic urticaria is chronic inducible urticaria.

38. The method of claim 26, wherein the chronic urticaria is chronic inducible urticaria.

39. The method of claim 27, wherein the chronic urticaria is chronic inducible urticaria.

40. A method of treating chronic inducible urticaria, comprising administering to a subject in need thereof the pharmaceutical composition of claim 18.

41. A method of treating chronic inducible urticaria, comprising administering to a subject in need thereof the pharmaceutical composition of claim 21.

42. A method of treating chronic inducible urticaria, comprising administering to a subject in need thereof the pharmaceutical composition of claim 24.

43. A process for making the crystalline form of claim 1, the process comprising:

a) reacting N-(3-(6-amino-5-(2-(methylamino) ethoxy) pyrimidin-4-yl)-5-fluoro-2-methylphenyl)-4-cyclopropyl-2-fluorobenzamide with at an acrylic anhydride in a non-chlorinated solvent, optionally in the presence of an inorganic base; and b) isolating the crystalline form as a solid.

44. The process according to claim 43, wherein the non-chlorinated solvent is ethyl acetate.

45. The process of claim 43, wherein the crystalline form is isolated from a suspension that results from distillation.

* * * * *